(12) United States Patent
Landfester et al.

(10) Patent No.: US 10,400,164 B2
(45) Date of Patent: Sep. 3, 2019

(54) LONG-TERM STABLE PHOTOACTIVE COMPOSITION, SUCH AS PHOSPHORESCENT COMPOSITION OR TTA-PHOTON UPCONVERSION COMPOSITION

(71) Applicant: MAX-PLANCK-GESELLSCHAFT ZUR FÖRDERUNG DER WISSENSCHAFTEN E.V., München (DE)

(72) Inventors: Katharina Landfester, Mainz (DE); Yuri Avlasevich, Mainz (DE); Andrey Turshatov, Griesheim (DE); Frederik Wurm, Mainz (DE); Mikhail Filatov, Mainz (DE); Dzmitry Busko, Mainz (DE); Stanislav Balouchev, Mainz (DE); Filippo Marsico, Mainz (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 453 days.

(21) Appl. No.: 15/022,056

(22) PCT Filed: Sep. 23, 2014

(86) PCT No.: PCT/EP2014/070225
§ 371 (c)(1),
(2) Date: Mar. 15, 2016

(87) PCT Pub. No.: WO2015/044129
PCT Pub. Date: Apr. 2, 2015

(65) Prior Publication Data
US 2016/0222286 A1    Aug. 4, 2016

(30) Foreign Application Priority Data
Sep. 24, 2013  (EP) ..................... 13185751

(51) Int. Cl.
*A61K 49/00* (2006.01)
*C09K 11/06* (2006.01)
*H01L 51/00* (2006.01)
*H01L 51/50* (2006.01)

(52) U.S. Cl.
CPC .......... *C09K 11/06* (2013.01); *A61K 49/0015* (2013.01); *C09K 2211/1007* (2013.01); *C09K 2211/1011* (2013.01); *C09K 2211/1029* (2013.01); *C09K 2211/185* (2013.01); *H01L 51/0003* (2013.01); *H01L 51/5016* (2013.01)

(58) Field of Classification Search
CPC ............ C09K 11/06; C09K 2211/1007; C09K 2211/1001; C09K 2211/1029; C09K 2211/185; H01L 51/5016
See application file for complete search history.

(56) References Cited

U.S. PATENT DOCUMENTS

2012/0001217 A1    1/2012  Kang et al.

FOREIGN PATENT DOCUMENTS

| DE | 102004063134 A1 | 7/2006 |
|----|-----------------|--------|
| EP | 2067839 A1      | 6/2009 |
| JP | H05190283 A     | 7/1993 |
| WO | 2012050137 A1   | 4/2012 |

OTHER PUBLICATIONS

Barbara Enko et al: "Singlet oxygen-induced photodegradation of the polymers and dyes in optical sensing materials and the effect of stabilizers on these processes", The Journal of Physical Chemistry A., vol. 117, No. 36, Sep. 12, 2013.

Schweitzer C. et al: "Physical mechanisms of generation and deactivation of singlet oxygen", Chemical Reviews, American Chemical Society, US, vol. 103, No. 5, Apr. 30, 2003.

(Continued)

*Primary Examiner* — C Melissa Koslow
(74) *Attorney, Agent, or Firm* — Cantor Colburn LLP

(57) ABSTRACT

A long-term stable photoactive composition, namely a phosphorescent composition or a TTA-photon upconversion composition, contains:
a) at least one compound, which has a triplet state capable of energy transfer via an emissive process or a non-emissive process, wherein the at least one compound having a triplet state is
  i) at least one phosphorescent compound and/or
  ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is capable of a triplet-triplet energy transfer to the at least one emissive compound and wherein the at least one emissive compound is preferably capable of a triplet-triplet annihilation, and
b) at least one compound capable of reacting with singlet oxygen, wherein the at least one compound capable of reacting with singlet oxygen comprises at least one terminal unsaturated carbon-carbon bond and is selected from the group consisting of compounds having anyone of the general formulae (I) to (X).

16 Claims, 4 Drawing Sheets

(56) References Cited

OTHER PUBLICATIONS

Young R. and Martin R.: "On the mechanism of quenching of singlet oxygen by amines"., Journal of the American Chemistry Society, vol. 94, No. 15, Jul. 26, 1972.
Aebisher et al., "Singlet Oxygen Chemistry in Water: A Porous Vycor GlassSupported Photosensitizer", Journal of Physical Chemistry Part B: Condensed Matter, Materials, Surfaces, Interfaces & Biophysical, vol. 112, No. 7, Feb. 1, 2008, pp. 1913-1917.
European Search Report from the European Patent Office for EP Application No. 14771896.9 dated Dec. 10, 2018, 5 pages.
Gollnick et al., "Merbromin (mercurochrome)—A photosensitizer for singlet oxygen reactions", Journal of Photochemistry and Photobiology B: Biology, Elsevier Science S.A., Basel, Ch, vol. 5, No. 1, Apr. 1, 1990, pp. 85-93.

LONG-TERM STABLE PHOTOACTIVE COMPOSITION, SUCH AS PHOSPHORESCENT COMPOSITION OR TTA-PHOTON UPCONVERSION COMPOSITION

CROSS-REFERENCES TO RELATED APPLICATIONS

This patent application claims the benefit of priority to European Patent Application Serial No. 13185751.8, filed Sep. 24, 2013 and International Application No. PCT/EP2014/070225 filed Sep. 23, 2014 which are incorporated herein by reference in their entirety.

The present invention relates to a long-term stable photoactive composition, namely a phosphorescent composition or a TTA-photon upconversion composition.

Photoactive compositions, such as phosphorescent compositions or photon upconversion compositions, are used in a plurality of applications, such as in organic light-emitting devices, solar cells, inks, thermal sensors, oxygen sensors, coating materials and the like. Both phenomena, phosphorescence and annihilation photon upconversion involve the excitation of triplet states in the concerned molecules after absorption of light and are characterized by the emission of light. While phosphorescent materials emit light having a lower frequency than that of the absorbed light, photon upconversion compositions emit light with a higher frequency than that of the absorbed light.

Phosphorescent molecules are excited by absorbed energy at first from the ground state into an excited singlet state. Thereafter, the excited singlet state non-radiatively transitions into an excited triplet state, which is called intersystem crossing. Thereby, the spin of the excited electron is reversed, so that the spin of the excited electron in the triplet state is no longer paired with the spin of the ground state electron. As a result thereof, the energy is trapped in the excited triplet state, because only classically forbidden transitions and thus kinetically unfavored transitions may lead to a return of the excited triplet state electron into the ground state with simultaneous emission of a photon. On account of this reason, the transition probability for the electron from the excited triplet state into the ground state is quite low, i.e. the triplet lifetime is comparable long and amounts—in dependency of the phosphorescent material—up to minutes or even hours. This is the reason for the well-known phenomenon that phosphorescent materials are characterized by an afterglow. Because the energy level of the excited triplet state of phosphorescent materials is lower than that of the excited singlet state, these materials emit light having a lower frequency than that of the absorbed light. Phosphorescent materials are—among others—used in thermal and oxygen sensors. The sensing process includes optical excitation of the phosphorescent molecules and registration of the decreased phosphorescence or phosphorescence decay time as a function of the increased sample temperature or oxygen content.

In contrast to phosphorescent materials, photon upconversion compositions emit light with a higher frequency than that of the absorbed light. This phenomenon is often associated with high light intensities, such as those available from pulsed lasers. The upconversion process involves the energy transfer of several lower excited states to a single higher excited state, which then emits light with a higher frequency, i.e. with higher energy. This process has been described not only for a number of inorganic systems in the solid state, including crystals, but also for thin films and nanoparticles. Typical photon upconversion compositions comprise a sensitizer compound, an emissive compound and a solvent or matrix compound, respectively.

In one of the known photon upconversion mechanism, which is called triplet-triplet annihilation upconversion (TTA-UC), the sensitizer compound absorbs light with a first frequency $v_1$, whereby the sensitizer compound is excited from the ground state into an excited singlet state. Thereafter, the excited singlet state non-radiatively transitions into an excited triplet state, i.e. undergoes an intersystem crossing. As a result thereof, the energy is trapped in the excited triplet state, because—as set out above—only kinetically unfavored transitions lead to a return of the excited triplet state into the ground state. Due to this, energy may be transferred from the sensitizer compound to the emissive compound by means of triplet-triplet energy transfer (TTET), e.g. by Dexter energy transfer. Due to this triplet-triplet energy transfer, the electron of the excited triplet state in the sensitizer compound returns into the ground state, whereas an electron from the ground state of the emissive compound is transferred into the excited triplet state. Two excited emissive molecules may then undergo a triplet-triplet annihilation (TTA), wherein the excited electron of one emissive molecule transfers its energy to the excited electron of the other emissive molecule. In other words, the excited electron of one emissive molecule returns from the excited triplet state into the ground state during the TTA, whereas the excited electron of the other molecule is transferred into a higher excited singlet state. Afterwards, the electron of the excited singlet state returns into the ground state of the emissive molecule, whereby light with a second frequency $v_2$ is emitted. Due to the energy shift on account of the TTA, the frequency $v_2$ of the emitted light is higher than the frequency $v_1$ initially absorbed by the sensitizer compound. This mechanism occur when the energy of the triplet state of the sensitizer compound and the triplet state of the emissive compound overlap.

When the energy of the triplet state of the emissive compound is much higher than that of the triplet state of the sensitizer compound, the mechanism of the TTA-UC is different to the above mentioned, because the TTA in this case already occurs in the sensitizer molecules.

A significant advantage of the TTA-UC is that it is independent from the coherence of the exciting light, so that TTA-UC occurs not only with a coherent light source, such as a laser, but also with non-coherent light, such as sunlight. Thus, only the light intensity and the wavelength of the light are decisive, wherein the range of absorbed wavelength can be increased by mixing different sensitizer compounds.

Due to their ability to convert that part of the sunlight with comparable long wavelengths to light having a shorter wavelength, TTA-UC compositions are particular promising materials for solar cells. Apart from that, TTA-UC compositions may be also used for high-resolution optical microscopy, solar harvesting, bioimaging, drug delivery, optical data storage, oxygen sensing and the like. As set out above, the TTA-UC compositions may include the sensitizer compound and emissive compound dispersed in a solvent or polymer matrix. Also known are TTA-UC nanoparticles or microparticles, in which the sensitizer and emissive compounds and solvent or matrix are for example encapsulated in a polymeric nano- or micro-container made for instance of polystyrene, polymethyl methacrylate or the like. Alternatively, the respective compounds may be encapsulated in non-ionic surfactant micelles.

One problem of known phosphorescent compositions or TTA-photon upconversion compositions is, however, that they are very sensitive to oxygen. This is due to the fact that oxygen is an effective quencher of excited triplet states. For example, in the presence of oxygen energy is efficiently transferred from the excited triplet state of the sensitizer compound to oxygen molecule, as a consequence of which oxygen is excited into singlet oxygen, whereas the sensitizer returns from the excited triplet state into the ground state. This reaction competes with the aforementioned triplet-triplet energy transfer from the sensitizer to the emissive compound and thus quenches the TTA-photon upconversion. Likewise, this reaction competes in phosphorescent compositions with the emission of light from the excited phosphorescent molecules and thus also quenches the phosphorescence. Apart from that, the formed singlet oxygen, which is highly reactive, oxidizes the sensitizer and emissive compounds and thus destroys the phosphorescent and TTA-UC compositions.

In order to overcome these problems, phosphorescent and TTA-UC compositions are usually degassed for example by bubbling molecular nitrogen through the solution or around the solid, in order to remove at least a part of the oxygen contained therein or in the surrounding atmosphere. These methods are, however, not satisfying, because they do not allow to remove all of the oxygen present in the composition or in the surrounding atmosphere. Moreover, at least some of these methods are time consuming and laborious.

Accordingly, the object underlying the present invention is to provide a composition containing at least one compound, which has a triplet state capable of energy transfer via an emissive process or a non-emissive process, which is effectively protected against the action of singlet oxygen and which can thus be used in ambient atmosphere.

According to the present invention this object is satisfied by providing a composition containing:
a) at least one compound, which has a triplet state capable of energy transfer via an emissive process or a non-emissive process, wherein the at least one compound having a triplet state is
  i) at least one phosphorescent compound and/or
  ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is preferably capable of a triplet-triplet energy transfer to the at least one emissive compound and wherein the at least one emissive compound is preferably capable of a triplet-triplet annihilation, and
b) at least one compound capable of reacting with singlet oxygen, wherein the at least one compound capable of reacting with singlet oxygen comprises at least one terminal unsaturated carbon-carbon bond and is selected from the group consisting of compounds having anyone of the following general formulae (I) to (X):

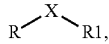
(I)

wherein

X is O or S,

R is alkenyl or alkynyl and

R1 is H, alkyl, ether-alkyl, ether-alkenyl, alkenyl, alkynyl, aralkyl, aryl or heteroaryl,

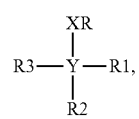
(II)

wherein

X is O or S,

R is alkenyl or alkynyl,

Y is alkyl, alkenyl, alkynyl, aralkyl, aralkenyl, aralkynyl, aryl or heteroaryl and R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

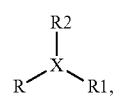
(III)

wherein

X is N or P,

R is alkenyl or alkynyl and

R1 and R2 are independently from each other H, alkyl, alkenyl, alkynyl, aralkyl, aryl or heteroaryl,

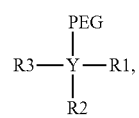
(IV)

wherein

PEG is an oligoethylene glycol or polyethylene glycol group having 2 to 99 ethylene glycol units, R1 is alkenyl or alkynyl, Y is Si and R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

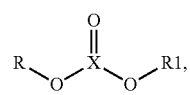
(V)

wherein

X is P, S, B or Si,

R is alkenyl or alkynyl and

R1 is H, alkyl, alkenyl, alkynyl, aralkyl, aryl or heteroaryl,

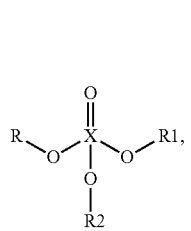

(VI)

wherein

X is P, S, B or Si,

R is alkenyl or alkynyl and

R1 and R2 are independently from each other H, alkyl, alkenyl, alkynyl, aralkyl, aryl or heteroaryl,

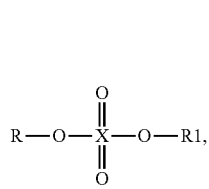

(VII)

wherein

X is P, S, B or Si,

R is alkenyl or alkynyl and

R1 is H, alkyl, alkenyl, alkynyl, aralkyl, aryl or heteroaryl,

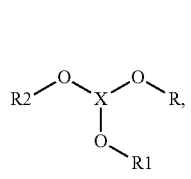

(VIII)

wherein

X is P, S, B or Si,

R is alkenyl or alkynyl and

R1 and R2 are independently from each other H, alkyl, alkenyl, alkynyl, aralkyl, aryl or heteroaryl,

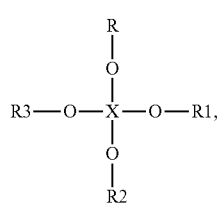

(IX)

wherein

X is P, S, B or Si,

R is alkenyl or alkynyl and

R1, R2 and R3 are independently from each other H, alkyl, alkenyl, alkynyl, aralkyl, aryl or heteroaryl,

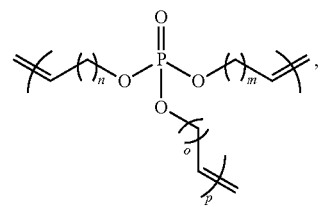

(Xa)

wherein n, m and o are independently from each other an integer between 1 and 20 and p is an integer of 2 or more,

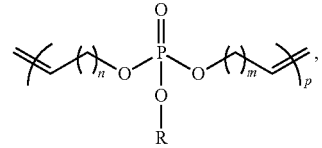

(Xb)

wherein

R is H, alkyl, alkenyl, alkynyl, aralkyl, aryl or heteroaryl, n and m are independently from each other an integer between 1 and 20 and p is an integer of 2 or more or

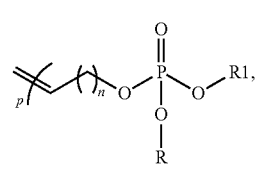

(Xc)

wherein

R and R1 are independently from each other H, alkyl, alkynyl, aralkyl, aryl or heteroaryl, n is an integer between 1 and 20 and p is an integer of 2 or more.

The compounds according to the aforementioned formulae (Xa) to (Xc) are generically sometimes below referred to as compounds according to the formula (X).

This solution is based on the surprising finding that by adding at least one of the aforementioned compounds comprising at least one terminal unsaturated carbon-carbon bond into the composition—preferably in high excess with regard to the at least one compound, which has a triplet state capable of energy transfer via an emissive process or a non-emissive process—the composition is effectively, completely and reliably protected against singlet oxygen. This is due to the fact that the aforementioned compounds comprising at least one terminal unsaturated carbon-carbon bond are capable to effectively and fast react with singlet oxygen, because the terminal unsaturated carbon-carbon bond is highly reactive with singlet oxygen. Due to this, the aforementioned compounds comprising at least one terminal unsaturated carbon-carbon bond are an efficient singlet oxygen inhibitor. More specifically, after the composition is subjected to light or other irradiation, the aforementioned compounds having the triplet state capable of energy transfer via an emissive process or a non-emissive process are excited and its triplet state is populated by electrons. Due to the initial presence of oxygen, some of the triplet states transfer energy to oxygen molecules, which leads to the generation of singlet oxygen. As set out above, the generated singlet oxygen reacts immediately and at least nearly exclusively with the singlet oxygen inhibitor, i.e. the at least one of the aforementioned compounds having terminal unsaturated carbon-carbon bonds, which results in an oxidization of the singlet oxygen inhibitor and thus in the consumption of the singlet oxygen. Consequently, after a short initial time span all oxygen molecules being initially present in the composition are consumed. Thereafter, the compound having a triplet state capable of energy transfer via an emissive process or a non-emissive process can work efficiently without being anymore affected by oxygen.

On account of all this, the composition in accordance with the present invention can be used for phosphorescence or TTA-UC at ambient conditions regardless of the oxygen content. A further advantage of the composition in accordance with the present invention is that it can be optimized easily concerning its properties as solvent and/or matrix material for the compound having a triplet state (such as with regard to its viscosity, hydrophobicity and solubility for the photoactive compounds) and concerning its impermeability against oxygen by appropriately selecting the length of the molecule chain with the terminal carbon-carbon bonds.

According to the present invention, a terminal unsaturated carbon-carbon bond is any unsaturated group according to the formula —CR═CH2 or —CR≡CH, irrespective of its location in the molecule. R may be H, alkyl, aryl, heteroaryl, alkenyl, alkynyl or aralkyl, either unsubstituted or substituted. Preferably, R is H, alkyl or aryl, more preferably R is H or a $C_{1-6}$-alkyl, even more preferably R is H or a $C_{1-3}$-alkyl, still more preferably R is H, methyl or ethyl and most preferably R is H.

Preferably, the at least one compound capable of reacting with singlet oxygen is not photochemically active and has in particular no triplet state capable of energy transfer via an emissive process or a non-emissive process.

As noted above, the present invention allows to protect a compound, which has a triplet state capable of energy transfer via an emissive process or a non-emissive process, from an unwanted reaction with singlet oxygen due to the presence of the at least one compound capable of reacting with singlet oxygen comprising at least one terminal unsaturated carbon-carbon bond. In order to particularly efficiently react with singlet oxygen, it is suggested in accordance with a preferred embodiment of the present invention that the composition contains as compound capable of reacting with singlet oxygen at least one compound, which comprises at least one terminal carbon-carbon double bond, because terminal carbon-carbon double bonds are more reactive with singlet oxygen than terminal carbon-carbon triple bonds.

In order to be present in a sufficient excess so as to allow to inactivate singlet oxygen over a long operation time, i.e. in order to have a particular high capacity for singlet oxygen inhibition, it is further preferred that the number of terminal unsaturated carbon-carbon bonds of the at least one compound capable of reacting with singlet oxygen is at least 100 times, more preferably at least 1,000 times, even more preferably at least 10,000 times, even more preferably at least $10^5$ times, still more preferably at least $10^6$, even more preferably at least $10^7$ times and most preferably at least $10^8$ times higher in the composition in accordance with the present invention than the number of molecules of all compounds having a triplet state capable of energy transfer via an emissive process or a non-emissive process. In this embodiments, the aforementioned compounds are included in the composition in a high excess with regard to the amount of all photoactive compounds, why singlet oxygen merely exclusively reacts with the singlet oxygen inhibitor and not or only to a minor degree with the photoactive compounds. Due to this only a small amount of the unsaturated carbon-carbon bonds of the singlet oxygen inhibitor is destroyed thereby, so that the composition still has a high capacity for singlet oxygen inhibition, so that oxygen penetrating or diffusing thereafter into the composition can be also reliably, effectively and fast consumed.

As noted above, the present invention allows to protect every phosphorescent compound and any triplet-triplet annihilation photon energy upconversion (TTA-UC) system from an unwanted reaction with singlet oxygen and in particular from an unwanted oxidization by singlet oxygen, which is formed from triplet oxygen due to energy transferred from the excited compound to oxygen present in the system. In particular, the present invention allows to protect phosphorescent substances from oxidization by singlet oxygen. Due to this, it is preferred that at least one of the at least one compound having a triplet state of the composition according to the present invention is a phosphorescent compound.

In principle, the present invention is not particularly limited concerning the chemical nature of the phosphorescent compound so that all phosphorescent compounds can be included in the composition according to the present invention. Good results are, however, in particular achieved, if one or more of the phosphorescent compounds described in detail later below are contained in the composition.

In order to assure that the singlet oxygen inhibitor, i.e. the at least one compound capable of reacting with singlet oxygen having at least one terminal unsaturated carbon-carbon bond, is present in a sufficient excess with regard to the at least one phosphorescent compound, so that it fast and efficiently reacts with singlet oxygen generated in the composition due to energy transfer from the at least one phosphorescent compound to oxygen (i.e. triplet oxygen), and thus protects the at least one phosphorescent compound from being oxidized by the singlet oxygen, it is preferred in the aforementioned embodiment that the composition comprises one or more phosphorescent compound(s) and at least one compound comprising at least one terminal unsaturated carbon-carbon bond, wherein the total concentration of all phosphorescent compounds in the composition is $1 \cdot 10^{-5}$ to $1 \cdot 10^{-3}$ mol/l, preferably $2.5 \cdot 10^{-5}$ to $7.5 \cdot 10^{-4}$ mol/l, more preferably $5 \cdot 10^{-5}$ to $5 \cdot 10^{-4}$ mol/l and most preferably about $1 \cdot 10^{-4}$ mol/l, and wherein the total content of all phosphorescent compounds and all compounds comprising at least one terminal unsaturated carbon-carbon bond in the composition is at least 90 mol-%, preferably at least 95 mol-%, more preferably at least 98 mol-%, even more preferably at least 99 mol-% and most preferably 100 mol-%.

More specifically, the present invention is excellently suited to protect phosphorescent systems from singlet oxygen. Accordingly, the composition of the present invention may consist of one or more phosphorescent compound(s)

and one or more compound(s) comprising at least one terminal unsaturated carbon-carbon bond, i.e. may consist exclusively of the phosphorescent compound(s) and singlet oxygen inhibitor(s) without needing any further ingredients.

In addition to phosphorescent compounds, the present invention is particularly suitable for the singlet oxygen inhibition in triplet-triplet annihilation photon energy upconversion (TTA-UC) systems. Due to this, the composition comprises according to a further preferred embodiment of the present invention at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$. In such a composition, the at least one sensitizer compound is preferably capable of a triplet-triplet energy transfer to the at least one emissive compound and the at least one emissive compound is preferably capable of a triplet-triplet annihilation.

In order to assure that the singlet oxygen inhibitor, i.e. the at least one compound capable of reacting with singlet oxygen comprising at least one terminal unsaturated carbon-carbon bond, is present in a sufficient excess with regard to the photoactive TTA-UC compounds, so that it fast and efficiently reacts with singlet oxygen generated in the composition due to energy transfer from the at least one sensitizer to oxygen (i.e. oxygen in triplet ground state), and thus protects the photoactive compounds from being oxidized by the singlet oxygen, it is preferred that the composition of this embodiment comprises at least one sensitizer compound, at least one emissive compound and at least one compound comprising at least one terminal unsaturated carbon-carbon bond, wherein the total concentration of all sensitizer compounds is $1 \cdot 10^{-5}$ to $1 \cdot 10^{-3}$ mol/l, wherein the total concentration of all emissive compounds is $1 \cdot 10^{-2}$ to $1 \cdot 10^{-4}$ mol/l, and wherein the total content of all sensitizer compounds, all emissive compounds and all compounds capable of reacting with singlet oxygen is at least 90 mol-%.

Even more preferably, the total concentration of all sensitizer compounds in the composition is $2.5 \cdot 10^{-5}$ to $7.5 \cdot 10^{-4}$ mol/l, still more preferably $5 \cdot 10^{-5}$ to $5 \cdot 10^{-4}$ mol/l and most preferably about $1 \cdot 10^{-4}$ mol/l, wherein the total concentration of all emissive compounds is preferably $5 \cdot 10^{-2}$ to $8 \cdot 10^{-3}$ mol/l, more preferably $9 \cdot 10^{-2}$ to $5 \cdot 10^{-3}$ mol/l and most preferably about $2 \cdot 10^{-3}$ mol/l, and wherein the total content of all sensitizer compounds, all emissive compounds and all compounds capable of reacting with singlet oxygen is preferably at least 95 mol-%, more preferably at least 98 mol-%, more preferably at least 99 mol-% and most preferably 100 mol-%.

Apart from the at least one sensitizer compound, from the at least one emissive compound and from the at least one singlet oxygen inhibitor compound, i.e. the at least one compound comprising at least one terminal unsaturated carbon-carbon bond, the composition of this embodiment may comprise further substances, such as solvents or the like. This is, however, not necessary, because the singlet oxygen inhibitor compound does simultaneously act as solvent for the sensitizer and emissive compound, as matrix for the sensitizer and emissive compound and as singlet oxygen inhibitor. Accordingly, it is preferred that the composition of this embodiment consists of one or more singlet oxygen inhibitor compound(s) comprising at least one terminal unsaturated carbon-carbon bond, one or more sensitizer compound(s) and one or more emissive compound(s). If, however, further substances, such as solvents, are used, these may be selected from the group consisting of toluene, tetrahydrofuran, acetonitrile, $C_{2-16}$-alkane (such as octane or hexadecane), polystyrene, oligostyrene and arbitrary combinations of two or more of these substances.

It is noted that all of the residues R and R1 to R3 described above with regard to the general formulae (I) to (X) as well as those described below with regard to other formulae comprise the respective residues in unsubstituted form as well as in substituted form.

In principle, all compounds falling under any of the general formulae (I) to (X) can be used as singlet oxygen inhibitor in the composition of the present invention, because all compounds falling under any of the general formulae (I) to (X) efficiently react on account of their terminal unsaturated carbon-carbon bond(s) excellently with singlet oxygen, and because they further provide good solvent properties. However, particularly good results are obtained, when the at least one compound capable of reacting with singlet oxygen has one of the aforementioned general formulae (I) to (III) and (V) to (IX), in which R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and preferably in which R is selected from the group consisting of allyl, 3-buten-1-yl, 4-penten-1-yl, 5-hexen-1-yl, 10-undecen-1-yl. Likewise, it is preferred when the at least one compound capable of reacting with singlet oxygen has the general formula (IV), in which R1 is selected from the above identified group. These residues have an appropriate chain length and degree of hydrophobicity leading to a very good reactivity with singlet oxygen, to a good solubility for phosphorescent and TTA-UC compounds as well as to a good impermeability to oxygen. Due to this, the singlet oxygen inhibitor is simultaneously a good solvent and matrix for the photoactive compounds.

As set out above, the singlet oxygen inhibitor included in the composition of the present patent application should have—apart from an excellent inhibition activity against singlet oxygen, i.e. apart from an excellent reactivity with singlet oxygen—a suitable hydrophobicity and a suitable viscosity, in order to also have excellent solvent and matrix properties for the at least one compound having a triplet state capable of energy transfer via an emissive process or a non-emissive process. In view of this, it is preferred that—if the at least one compound capable of reacting with singlet oxygen has the general formula (I) or the general formula (II)—X is oxygen or sulfur, R is alkenyl (preferably one of the aforementioned preferred one) and R1 in formula (I) or Y, R1, R2, R3 in formula (II), respectively, are as defined above for formulae (I) and (II).

Even better results are obtained with this regard, if the at least one compound capable of reacting with singlet oxygen in the composition has the general formula (I), in which X is oxygen, R is alkenyl and R1 is H, $C_{1-6}$-alkyl or $(CH_2)_n$—O—$(CH_2)_m$, wherein m and n are independently from each other integers of 1 or more.

Notably good results are obtained in this embodiment, when the composition contains as at least one of the at least one compound capable of reacting with singlet oxygen one having the general formula (I), in which X is oxygen, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 is H, $C_{1-6}$-alkyl or $(CH_2)_n$—$O(CH_2)_m$, wherein m and n are independently from each other integers of 1 to 6.

Most preferably, in the embodiment, in which the at least one compound capable of reacting with singlet oxygen has the general formula (I), X is oxygen, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 is H. One particular preferred example therefor is 5-hexene-1-ol.

In view of the suitable hydrophobicity, suitable viscosity and suitable oxygen impermeability of the singlet oxygen inhibitor, it is even more preferred that the composition in accordance with the present invention contains as at least one of the at least one compound capable of reacting with singlet oxygen a compound having the general formula (II), in which X is oxygen, R is alkenyl, Y is $C_{1-6}$-alkyl, $C_{6-12}$-aryl or $C_{6-12}$-heteroaryl and R1, R2, R3 are independently from each other H, XR, alkyl, ether-alkyl, ether-alkenyl, alkenyl or alkynyl, wherein X is oxygen and R is alkenyl.

Particular preferably, in the at least one compound capable of reacting with singlet oxygen and having the general formula (II) X is oxygen, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, Y is $C_{1-6}$-alkyl or phenyl and R1, R2, R3 are independently from each other H and XR, wherein X is oxygen and R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

In particular in the case that one or preferably two or three of residues R1, R2, R3 in the general formula (II) are XR, wherein X is oxygen and R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, a compound having not only a comparable high amount of double bonds per molecule and thus allowing to efficiently react with singlet oxygen, but also having a sufficiently high content of hydrophobicity and viscosity allowing the compound to be also a good solvent for the at least one photoactive compound is obtained.

Suitable examples for singlet oxygen inhibitors according to the aforementioned embodiments having the general formula (I) or the general formula (II) include substances selected from the group consisting of 3-butene-1-ol, 4-pentene-1-ol, 5-hexene-1-ol, 6-heptene-1-ol, 7-octene-1-ol, 1,2-di-(3-buten-1-yloxy)ethane, 1,2-di-(4-penten-1-yloxy)ethane, 1,2-di-(5-hexen-1-yloxy)ethane, 1,2-di-(6-hepten-1-yloxy)ethane, 1,2-di-(7-octen-1-yloxy)ethane, 1,2-di-(3-buten-1-yloxy)benzene, 1,2-di-(4-penten-1-yloxy)benzene, 1,2-di-(5-hexen-1-yloxy)benzene, 1,2-di-(6-hepten-1-yloxy)benzene, 1,2-di-(7-octen-1-yloxy)benzene, 1,3,5-tri-(3-buten-1-yloxy)benzene, 1,3,5-tri-(4-penten-1-yloxy)benzene, 1,3,5-tri-(5-hexen-1-yloxy)benzene, 1,3,5-tri-(6-hepten-1-yloxy)benzene, 1,3,5-tri-(7-octen-1-yloxy)benzene and arbitrary combinations of two or more of these compounds.

Notably good results are for example obtained with the following substances according to formula (I) or formula (II):

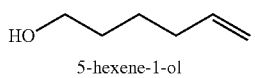
5-hexene-1-ol

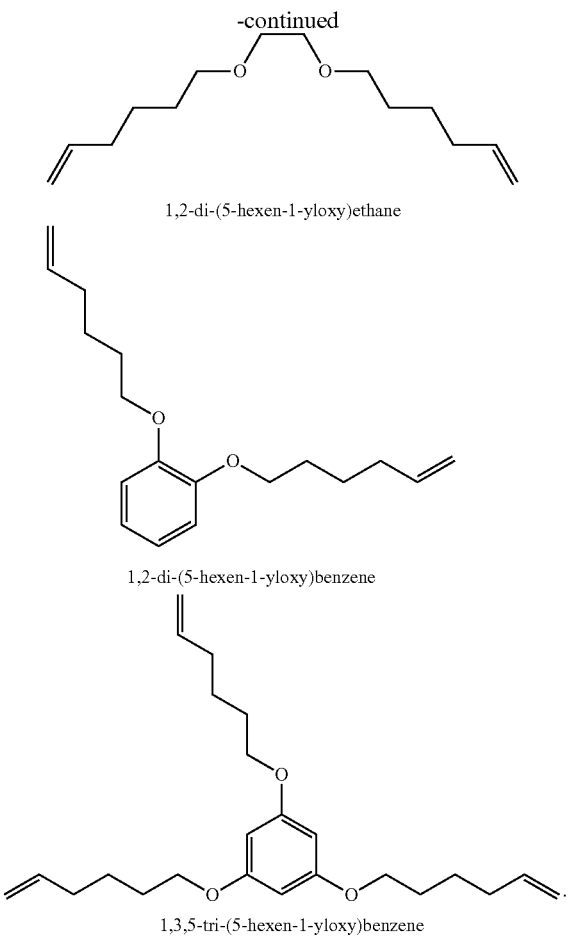
1,2-di-(5-hexen-1-yloxy)ethane 1,2-di-(5-hexen-1-yloxy)benzene 1,3,5-tri-(5-hexen-1-yloxy)benzene.

In an alternative embodiment of the present invention, the composition in accordance with the present invention includes as compound capable of reacting with singlet oxygen an unsaturated amine or phosphine, namely at least one compound having the general formula (III), wherein X is preferably nitrogen or phosphorus, R is preferably alkenyl and R1 and R2 are independently from each other preferably H or alkenyl.

More preferably, the at least one compound capable of reacting with singlet oxygen has the general formula (III), wherein X is phosphorus, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 and R2 are independently from each other H or selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

In particular in the case that the composition in accordance with the present invention includes as compound capable of reacting with singlet oxygen at least one compound having the general formula (III), wherein X is phosphorus and R, R1 and R2 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, the singlet oxygen inhibitor has a comparable high amount of double bonds per molecule allowing it to efficiently react with singlet oxygen and having a high singlet oxygen inhibition capacity as well as a sufficiently high content of hydrophobicity and viscosity allowing the compound to be also a good solvent for the at least one photoactive compound, which has a triplet state capable of energy transfer via an emissive process or a non-emissive process.

A particular suitable example for a singlet oxygen inhibitor having the general formula (III) is

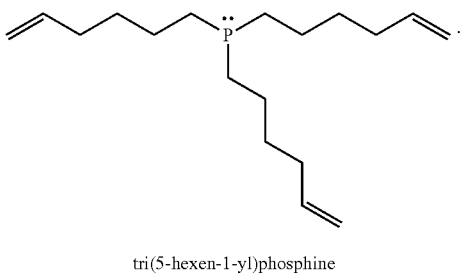

tri(5-hexen-1-yl)phosphine

In a further alternative embodiment of the present invention, the composition in accordance with the present invention includes as compound capable of reacting with singlet oxygen an unsaturated ethylene glycol unit comprising compound, namely at least one compound having the general formula (IV), in which PEG is an oligoethylene glycol or polyethylene glycol group having 2 to 99 ethylene glycol units, R1 is alkenyl, Y is Si and R2, R3 are independently from each other H, COOR, alkyl, alkenyl, alkynyl, aryl, heteroaryl or XR4, wherein X is N or P and R, R4 are independently from each other alkenyl.

Notably good results are in particular obtained, when the composition includes as compound capable of reacting with singlet oxygen at least one compound having the general formula (IV), in which R1 is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, Y is Si and R2, R3 are independently from each other H, COOR, XR4 or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, wherein X is N or P and R, R4 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

In an alternative and particularly preferred embodiment of the present invention, the composition in accordance with the present invention includes as compound capable of reacting with singlet oxygen at least one ester compound having any of the general formulae (V) to (IX), wherein X is P, S, B or Si, R is alkenyl and R1, R2 and R3 are independently from each other H, $C_{1-10}$-alkyl, $C_{1-10}$-alkenyl, $C_{6-18}$-alkylaryl or $C_{6-12}$-aryl.

More preferably, the at least one compound capable of reacting with singlet oxygen has any of the general formulae (V) to (IX), wherein X is P, S, B or Si, R is alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1, R2 and R3 are independently from each other H, $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Such compounds do not only have an excellent reactivity with singlet oxygen, but also have a suitable hydrophobicity and a suitable viscosity, so that they are excellent singlet oxygen inhibitors as well as excellent solvents for a compound having a triplet state capable of energy transfer via an emissive process or a non-emissive process.

Even more preferably, the at least one compound capable of reacting with singlet oxygen has any of the general formulae (V) to (IX), wherein X is P, S, B or Si, R is alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1, R2 and R3 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Even more preferably, R1, R2 and R3 are independently from each other phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and still more preferably, R1, R2 and R3 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Such compounds do not only have an excellent reactivity with singlet oxygen, but also have a suitable hydrophobicity and a suitable viscosity, so that they are excellent singlet oxygen inhibitors as well as excellent solvents for a compound having a triplet state capable of energy transfer via an emissive process or a non-emissive process.

Particular good results are obtained with this regard, when the compound capable of reacting with singlet oxygen has the general formula (VII), wherein X is S, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 is $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

Even better results are obtained with this regard, when the compound capable of reacting with singlet oxygen has the general formula (VI), wherein X is P, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, and R1 and R2 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Even more preferably, R1 and R2 are independently from each other phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and still more preferably, R1 and R2 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Such phosphate and silicate compounds do not only have an excellent reactivity with singlet oxygen and a high singlet oxygen inhibition capacity, but also have a suitable hydrophobicity and a suitable viscosity, so that they are excellent singlet oxygen inhibitors as well as excellent solvents for compounds having a triplet state capable of energy transfer via an emissive process or a non-emissive process, and a good impermeability to oxygen, so that the diffusion of oxygen into the composition is low.

According to still another preferred embodiment of the present invention, the composition in accordance with the present invention contains as compound capable of reacting with singlet oxygen at least one compound, which has the general formula (VIII), wherein X is B, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 and R2 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Even more preferably, R1 and R2 are independently from each other phenyl or alkenyl selected from the group consisting of allyl, 3-buten-1-yl, 4-penten-1-yl, 5-hexen-1-yl, 6-hepten-1-yl, 7-octen-1 yl, 8-nonen-1-yl, 9-decen-1-yl and 10-undecen-1-yl and still more preferably, R1 and R2 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Likewise to the aforementioned phosphate compounds, such borate compounds also have a good reactivity with singlet oxygen, a good impermeability to oxygen, a suitably high hydrophobicity as well as a suitable viscosity.

According to still another preferred embodiment of the present invention, the composition in accordance with the present invention contains as compound capable of reacting with singlet oxygen at least one compound, which has the general formula (IX), wherein X is Si, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1, R2 and R3 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Even more preferably, R1, R2 and R3 are independently from each other phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and still more preferably, R1, R2 and R3 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Likewise to the aforementioned phosphate and borate compounds, such silicate compounds also have a good reactivity with singlet oxygen, a good impermeability to oxygen, a suitably high hydrophobicity as well as a suitable viscosity.

Suitable individual examples for compounds according to the general formulae (V) to (IX) are compounds selected from the group consisting of:

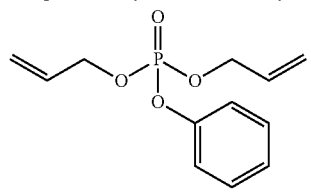

diallyl phenyl phosphate

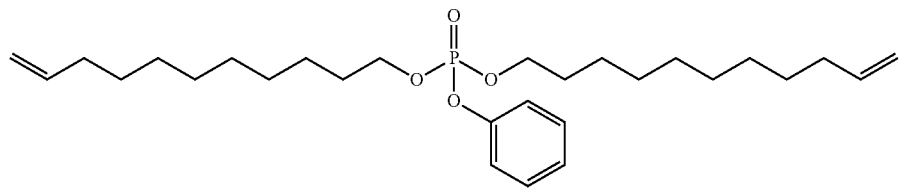

di(10-undecenyloxy) phenyl phosphate

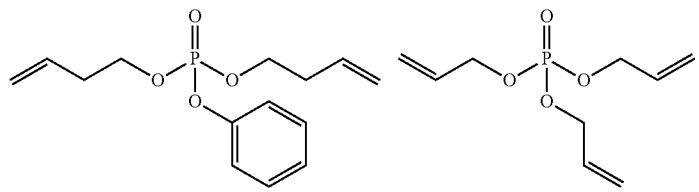

di(3-buten-1-yl) phenyl phosphate          triallyl phosphate

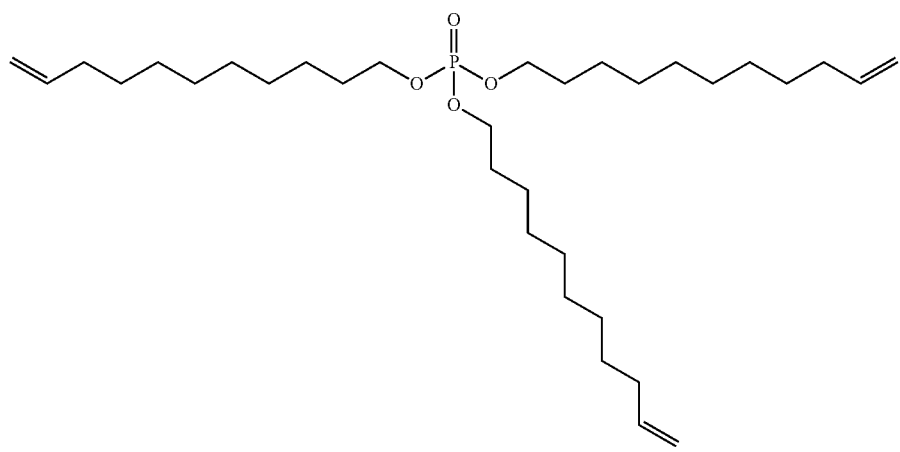

tri(10-undecen-1-yl) phosphate

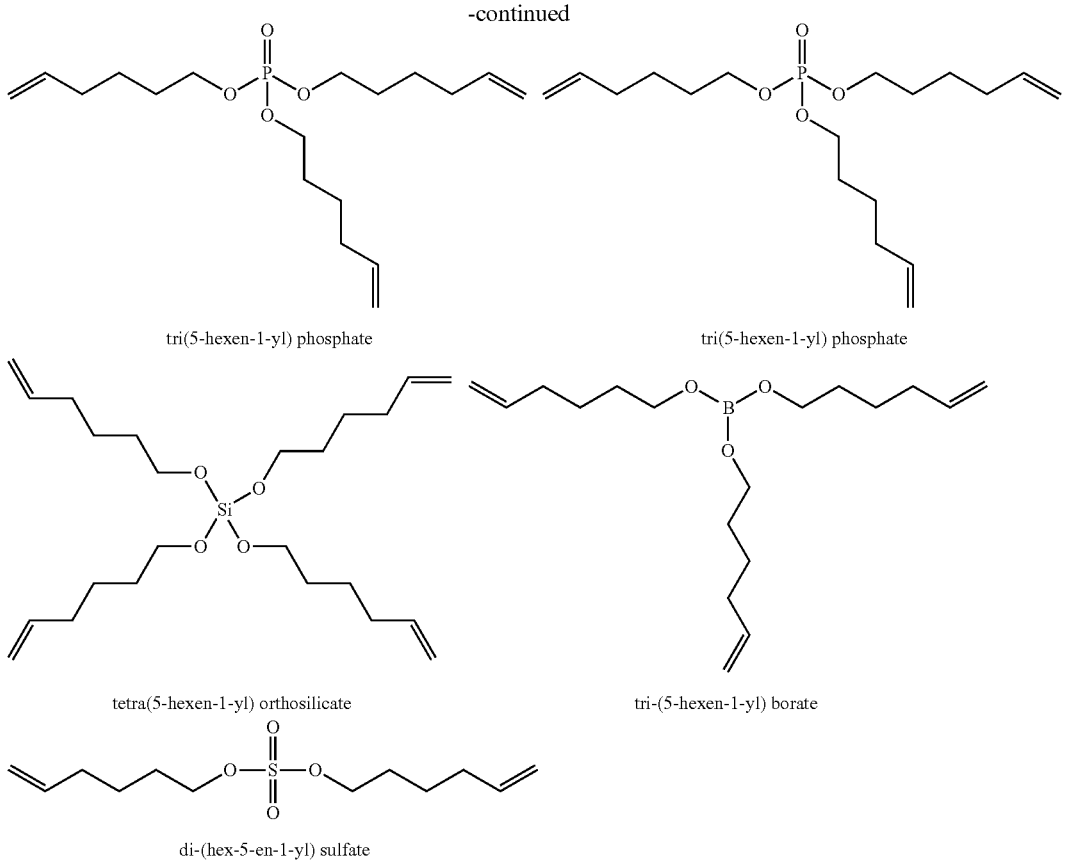

tri(5-hexen-1-yl) phosphate tri(5-hexen-1-yl) phosphate tetra(5-hexen-1-yl) orthosilicate tri-(5-hexen-1-yl) borate di-(hex-5-en-1-yl) sulfate and arbitrary combinations of two or more of these compounds.

According to a further, even more preferred embodiment of the present patent application, the composition contains as compound capable of reacting with singlet oxygen at least one compound according to the general formula (Xa), wherein n, m and o are independently from each other an integer between 1 and 10 and p is an integer of 2 to 120, or according to the general formula (Xb), wherein R is an aryl and preferably a phenyl, n and m are independently from each other an integer between 1 and 10 and p is an integer of 2 to 120, or according to the general formula (Xc), wherein R and R1 are independently from each other an aryl and preferably a phenyl, n is an integer between 1 and 10 and p is an integer of 2 to 120. Such hyperbranched phosphoester compounds do not only have a sufficiently high degree of hydrophobicity and viscosity allowing the compound to be a good solvent for the at least one compound, but also provide a very high number of double bonds per molecule, which are able to react with singlet oxygen, so that these compounds are also very effective singlet oxygen inhibitors and have a high singlet oxygen inhibition capacity.

Moreover, these hyperbranched phosphoester compounds act as excellent matrix material for the at least one compound, which has a triplet state capable of energy transfer via an emissive process or a non-emissive process. In addition, these hyperbranched phosphoester compounds have an excellent impermeability to oxygen, so that oxygen only diffuses into the composition—if at all—in an insignificant extent. In addition to terminal carbon-carbon double bonds, these compounds also comprise internal carbon-carbon double bonds. Due to all these properties, the compounds according to the general formula (X) and in particular those according to the general formula (Xa), in which n, m and o are independently from each other integers between 1 and 10 and p is an integer of 2 to 120, are most preferred ingredients of the composition in accordance with the present patent application.

Preferably, m, n and o are an integer between 2 and 11 and even more preferably m, n and o are an integer between 4 and 11 in the aforementioned formula (Xa). Likewise to this, m and n are preferably an integer between 2 and 11 and even more preferably m and n are an integer between 4 and 11 in the aforementioned formula (Xb). Likewise to this, n is preferably an integer between 2 and 11 and even more preferably n is an integer between 4 and 11 in the aforementioned formula (Xc).

Notably good results are obtained, when p is an integer between 3 and 40 in the aforementioned formulae (Xa), (Xb) and (Xc).

Furthermore, the hyperbranched phosphoester compounds according to any of the formulae (Xa), (Xb) and (Xc) have preferably a total number of terminal unsaturated carbon-carbon bonds per molecule of 4 or more, more preferably between 4 and 122 and even more preferably between 5 and 42.

According to a further particular preferred embodiment of the present invention, the composition contains as compound capable of reacting with singlet oxygen at least one compound according to the general formula (Xa), wherein n, m and o are independently from each other an integer between 4 and 11 and p is an integer of 3 to 40.

Notably good examples of these compounds are:

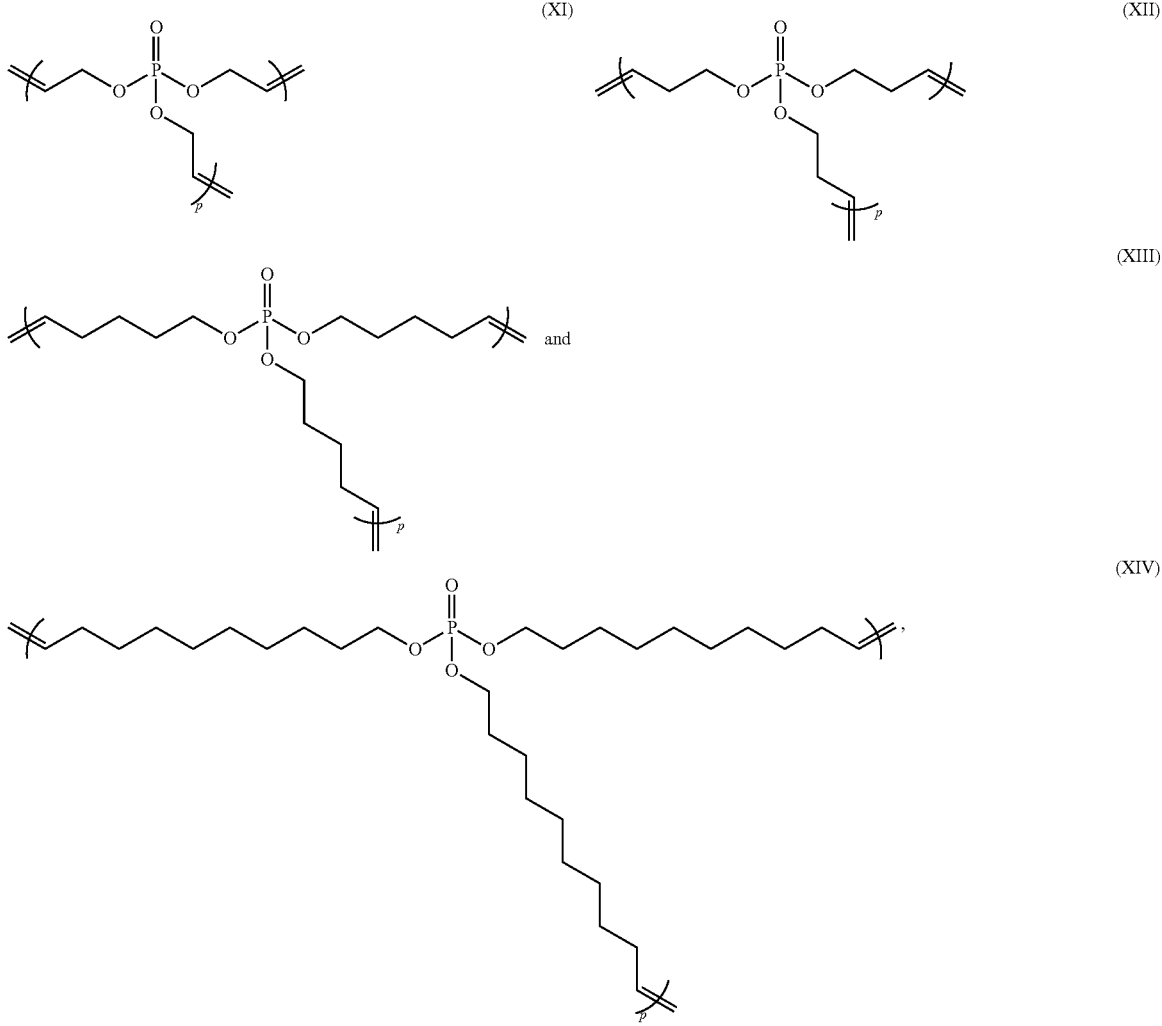

wherein in each of these formulae p is an integer of 2 to 120 and preferably p is an integer of 3 to 40.

In view of a high content of double bonds per molecule, an optimal hydrophobicity and viscosity and an optimal action as matrix material for the at least one compound, which has a triplet state capable of energy transfer via an emissive process or a non-emissive process, the singlet oxygen inhibitor of the composition in accordance with a particular preferred embodiment of the present patent application is a compound according to any of the formulae (Xa) to (Xc) and particularly preferably a compound according to the formula (Xa) having a number average molecular weight determined by gel permeation chromatography (GPC) of 500 to 50,000 g/mol. According to the present invention, the GPC measurement for determining the number average molecular weight is carried out in dimethylformamide (DMF) or in tetrahydrofuran (THF) with samples having a concentration of 1 g/l. The sample injection is performed with a 717 plus auto sampler from Waters Corporation at 30° C. in THF, whereas the flow is 1 ml/min. In DMF, three GRAM columns of the company PSS GmbH & Co. KG with the dimensions 300×80 mm, 10 μm particle size with respective pore sizes of 106, 104 and 103 Å are employed, whereas in THF three SDV columns of the company PSS GmbH & Co. KG with the dimensions 300×80 mm, 10 μm particle size and pore sizes of 106, 104 and 500 Å are employed. The Detection is accomplished with a DRI Shodex RI-101 detector of the company ERC Incorporation and with an UV-Vis S-3702 detector of the company Soma Co. Ltd. and the calibration is carried out using polystyrene standards provided by the company PSS GmbH & Co. KG.

The number of terminal unsaturated carbon-carbon bonds in such hyperbranched phosphoester compounds can be determined by using GPC, $^1$H-nuclear magnetic resonance (NMR) spectroscopy and size-exclusion chromatography (SEC). This is due to the fact that the peaks of terminal olefinic bonds are located in the $^1$H-NMR spectrum at 5.8 and at 5.1 to 5.2 ppm, respectively, whereas the peaks of the internal olefinic bonds are located at about 5.5 ppm. Thus, from the integral ratio of these resonances—combined with SEC analysis proving that no residual monomer is present in the system and after determining the molecular weight of the polymer—one can determine the number of terminal double bonds per polymer molecule. More specifically, the number average molecular weight of the hyperbranched phosphoester compound is determined by GPC, which is performed as described above. From the number average molecular weight of the hyperbranched phosphoester compound, the degree of polymerization (DP) is calculated. Moreover, from the ¹H-NMR spectrum the number of rings formed in the hyperbranched phosphoester is determined. Then, the number of terminal carbon-carbon double bonds in the molecule is determined according to the following formula:

$$n_{terminal\ C=C} = DP + 2 - n_{cylces},$$

wherein $n_{cycles}$ is the number of rings in the molecule.

In principle, as sensitizer compound or phosphorescent compound, respectively, all substances known to a person skilled in the art as sensitizer compound or phosphorescent compound can be applied in the composition in accordance with the present invention, provided that they can be dissolved in a sufficient extent in the singlet oxygen inhibitors, i.e. compounds capable of reacting with singlet oxygen preferably having one of the general formulae (I) to (X).

Taking the aforementioned requirements into account, the composition in accordance with the present invention preferably comprises as emissive compound at least one substituted or unsubstituted polycyclic aromatic compound.

Preferably, the composition in accordance with the present invention comprises as the at least one polycyclic hydrocarbon compound a compound according to the general formula (XV):

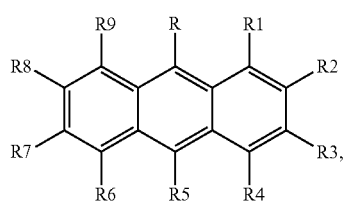

(XV)

wherein
R and R1 to R9 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, and/or neutral groups, such as polyethylene glycol or polyvinyl alcohol chains.

If necessary, one or more of the residues R and R1 to R9 of the emissive compound according to the general formula (XV) are substituted with linear or branched alkyl groups for better solubility in the solvent, i.e. in the singlet oxygen inhibiting compound preferably having anyone of the general formulae (I) to (X), with negatively charged groups for water solubility, such as sulfate or carboxyl, with positively charged groups for water solubility, such as ammonium, and/or with neutral water-solubilizing groups, such as or polyvinyl alcohol chains.

Even better results are obtained, when the composition in accordance with the present invention includes as the at least one polycyclic hydrocarbon compound a compound according to the general formula (XV), in which one to five of R and R1 to R9 are independently from each other aralkyl, aralkenyl, aralkinyl or aryl, whereas the remaining of R and R1 to R9 are hydrogen or $C_{1-10}$-alkyl.

Preferably, in the general formula (XV) one to four residues R and R1 to R9 are phenyl, whereas the remaining residues are hydrogen.

Exemplarily, notably good results are obtained, when the composition in accordance with the present invention contains as emissive compound at least one polycyclic hydrocarbon compound according to any of the subsequent formulae:

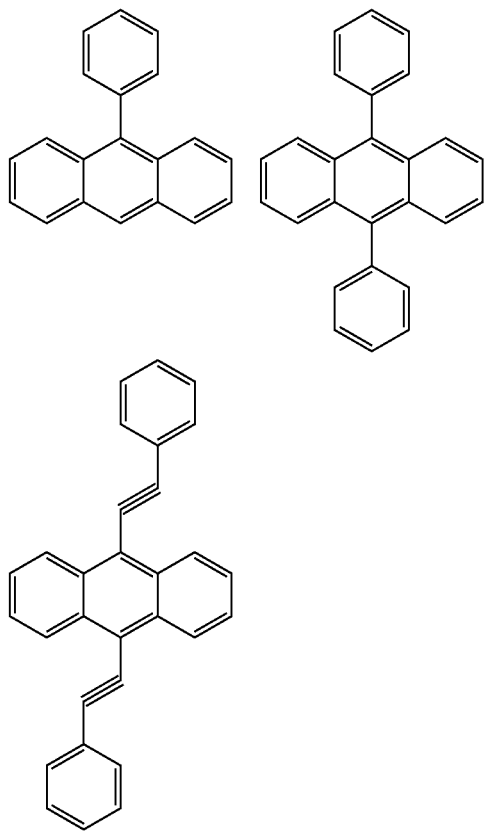

According to an alternative embodiment, the composition in accordance with the present invention contains as the emissive compound at least one polycyclic hydrocarbon according to the general formula (XVI):

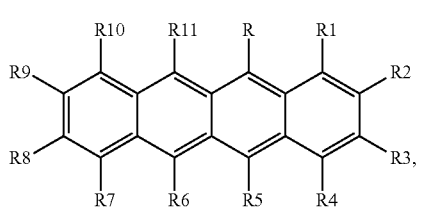

(XVI)

wherein
R and R1 to R11 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XVI), in which one to five of R and R1 to R11 are independently from each other aralkyl, aralkenyl, aralkinyl or aryl, whereas the remaining of R and R1 to R11 are hydrogen or $C_{1-10}$-alkyl.

Preferably, in the general formula (XV) one to four residues R and R1 to R11 are phenyl, whereas the remaining residues are hydrogen.

Exemplarily, notably good results are obtained, when the composition in accordance with the present invention contains as emissive compound at least one polycyclic hydrocarbon compound according to any of the subsequent formulae:

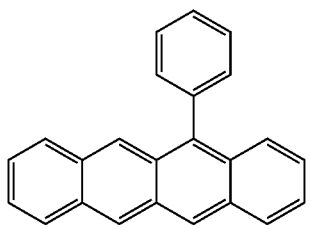

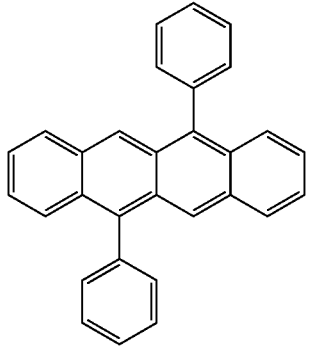

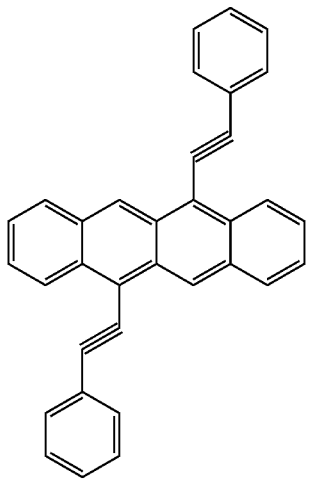

-continued

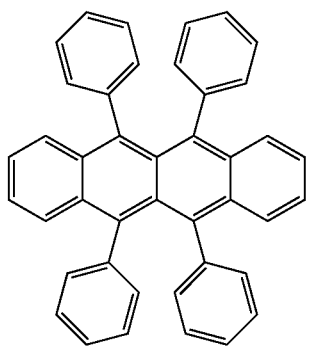

According to still an alternative embodiment, the composition in accordance with the present invention contains as the emissive compound at least one polycyclic hydrocarbon according to the general formula (XVII):

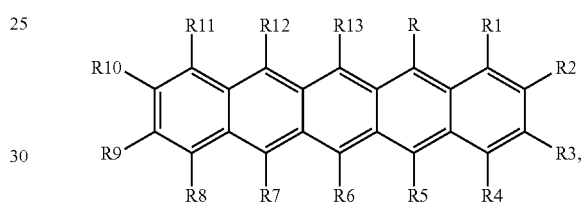

(XVII)

wherein

R and R1 to R13 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XVII), in which one to five of R and R1 to R13 are independently from each other aralkyl or aryl, whereas the remaining of R and R1 to R13 are hydrogen, More preferably, the composition contains as the at least one polycyclic hydrocarbon compound a compound according to the general formula (XVII), in which one to four aralkyl or aryl and even more preferably triflouromethylphenyl, whereas the remaining of R and R1 to R13 are hydrogen.

Exemplarily, notably good results are obtained, when the composition in accordance with the present invention contains as emissive compound at least one polycyclic hydrocarbon compound according to the following formula:

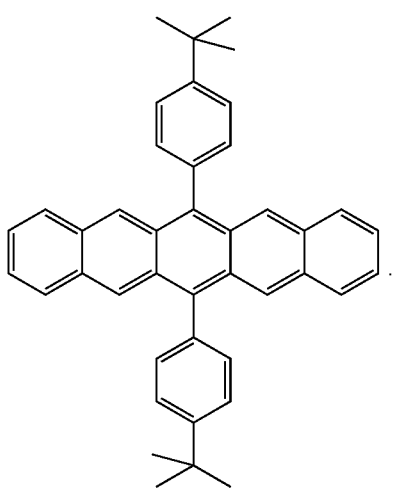 [SMILES: CC(C)(C)c1ccc(-c2c3cc4ccccc4cc3c(-c3ccc(C(C)(C)C)cc3)c3cc4ccccc4cc23)cc1]

According to still an alternative embodiment, the composition in accordance with the present invention contains as the emissive compound at least one polycyclic hydrocarbon according to the general formula (XVIII):

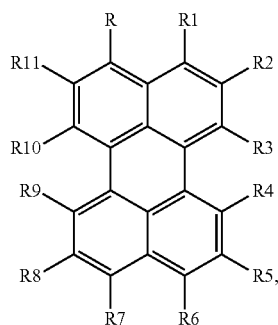

(XVIII)

wherein
R and R1 to R11 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XVIII), in which one to four of R and R1 to R11 are independently from each other a carboxylic ester group, aralkyl, aralkenyl, aralkinyl or aryl, whereas the remaining of R and R1 to R11 are hydrogen or $C_{1-10}$-alkyl. More preferably, in the general formula (XVIII) one to four of R and R1 to R11 are independently from each other a carboxylic ester group, aralkyl or aralkinyl, whereas the remaining of R and R1 to R11 are hydrogen. Even more preferably, in the general formula (XVIII) one to four of R and R1 to R11 are independently from each other an $C_{1-6}$-carboxylic ester group, triflourophenyl group or triflourophenylethynylene group, whereas the remaining of R and R1 to R11 are hydrogen.

Exemplarily, notably good results are obtained, when the composition in accordance with the present invention contains as emissive compound at least one polycyclic hydrocarbon compound according to any of the following formulae:

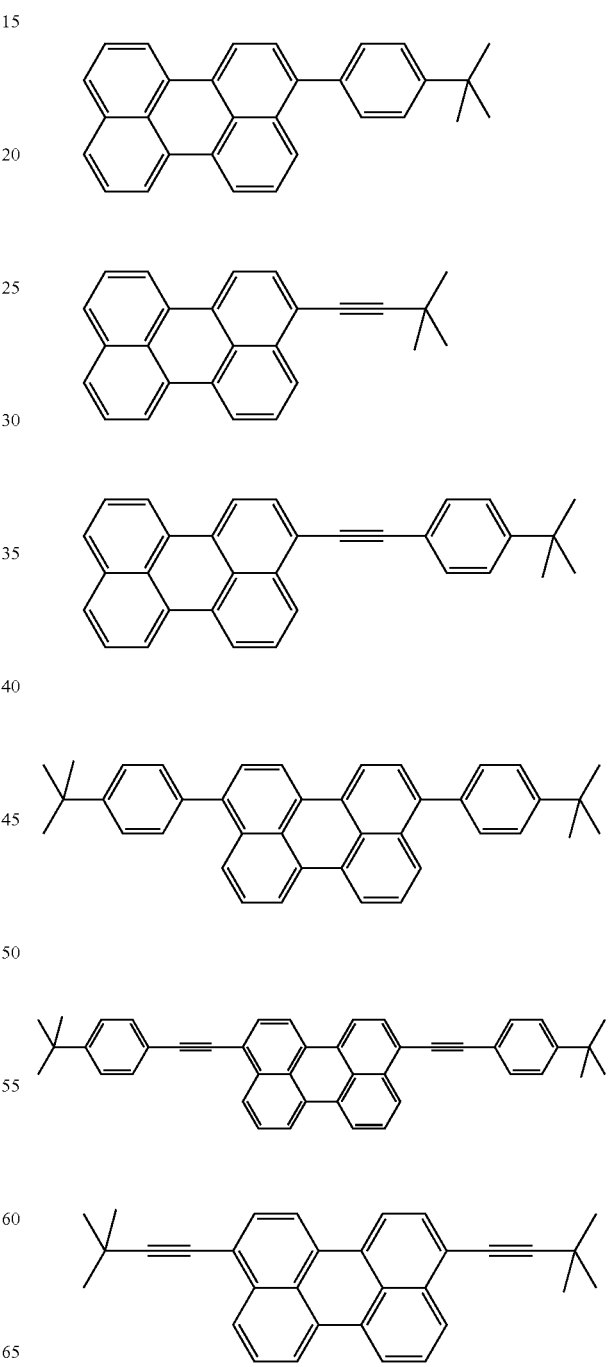

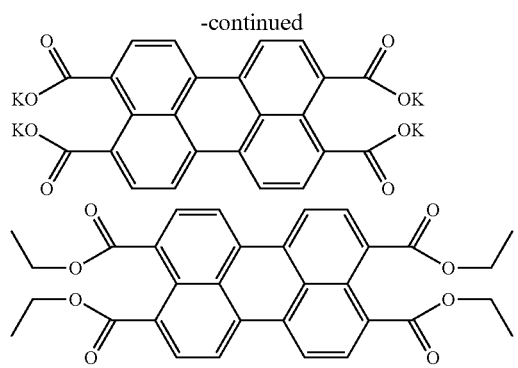

According to still an alternative embodiment, the composition in accordance with the present invention contains as the emissive compound at least one polycyclic hydrocarbon according to the general formula (XIX):

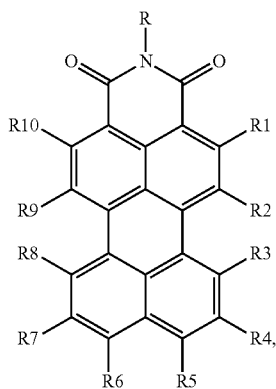

(XIX)

wherein
R is alkyl or aryl and
R1 to R10 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XIX), in which one to four of R and R1 to R10 are independently from each other aralkyl, aralkenyl, aralkinyl or aryl, whereas the remaining of R and R1 to R10 are hydrogen or $C_{1-10}$-alkyl. Even more preferably, in the general formula (XIX) one to four of R and R1 to R10 are independently from each other aralkyl and/or aralkinyl, whereas the remaining of R and R1 to R10 are hydrogen. More specifically, in the general formula (XIX) one to four of R and R1 to R10 are independently from each other triflouromethyl phenyl and/or triflouromethyl ethynylene, whereas the remaining of R and R1 to R10 are hydrogen.

Exemplarily, notably good results are obtained, when the composition in accordance with the present invention contains as emissive compound at least one polycyclic hydrocarbon compound according to any of the following formulae:

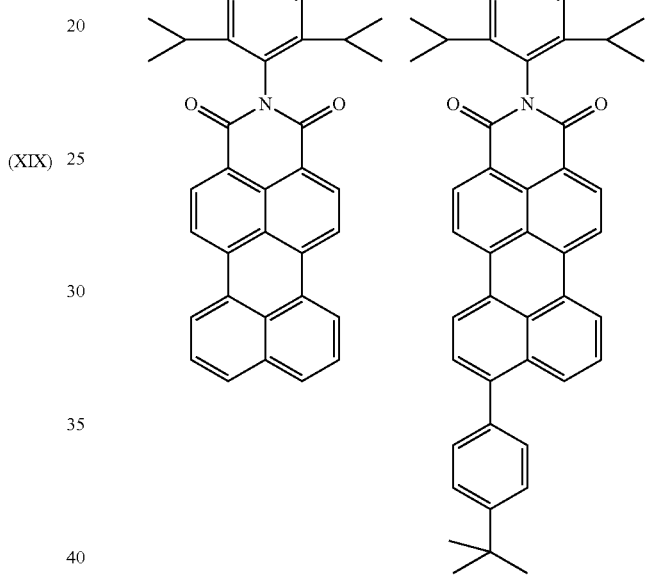

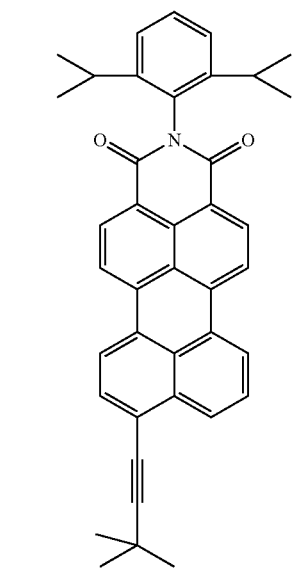

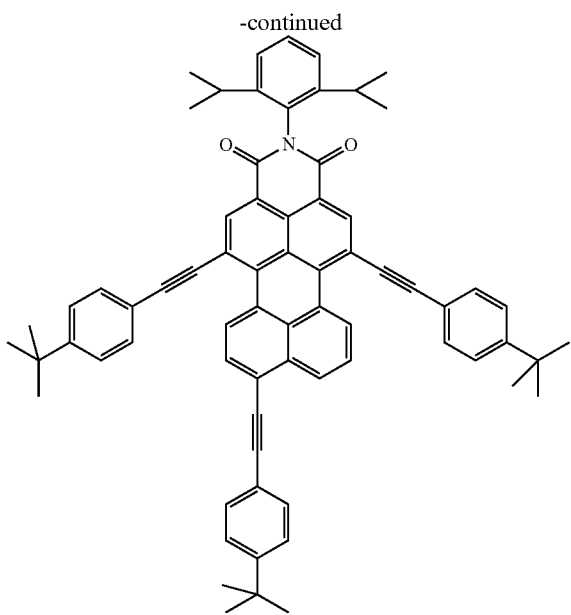

According to still an alternative embodiment, the composition in accordance with the present invention contains as the emissive compound at least one polycyclic hydrocarbon according to the general formula (XX):

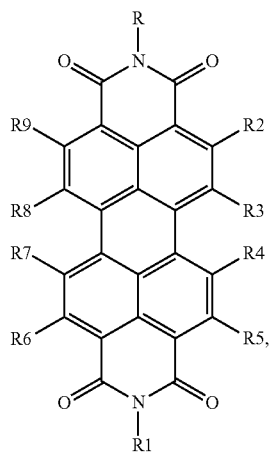

(XX)

wherein
R and R1 are independently from each other alkyl or aryl and
R2 to R9 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XX), in which one to four of R and R1 to R9 are independently from each other aralkyl, aralkenyl, aralkinyl or aryl, whereas the remaining of R and R1 to R9 are hydrogen or $C_{1-10}$-alkyl. More preferably, in the general formula (XIX) one to four of R and R1 to R9 are independently from each other aralkyl, aralkenyl, aralkinyl or aryl, whereas the remaining of R and R1 to R9 are hydrogen or $C_{1-10}$-alkyl. Even more preferably, in the general formula (XX) one to four of R and R1 to R9 are independently from each other trifluorophenyl and/or trifluoroethynyl, whereas the remaining of R and R1 to R9 are hydrogen.

Exemplarily, notably good results are obtained, when the composition in accordance with the present invention contains as emissive compound at least one polycyclic hydrocarbon compound according to any of the following formulae:

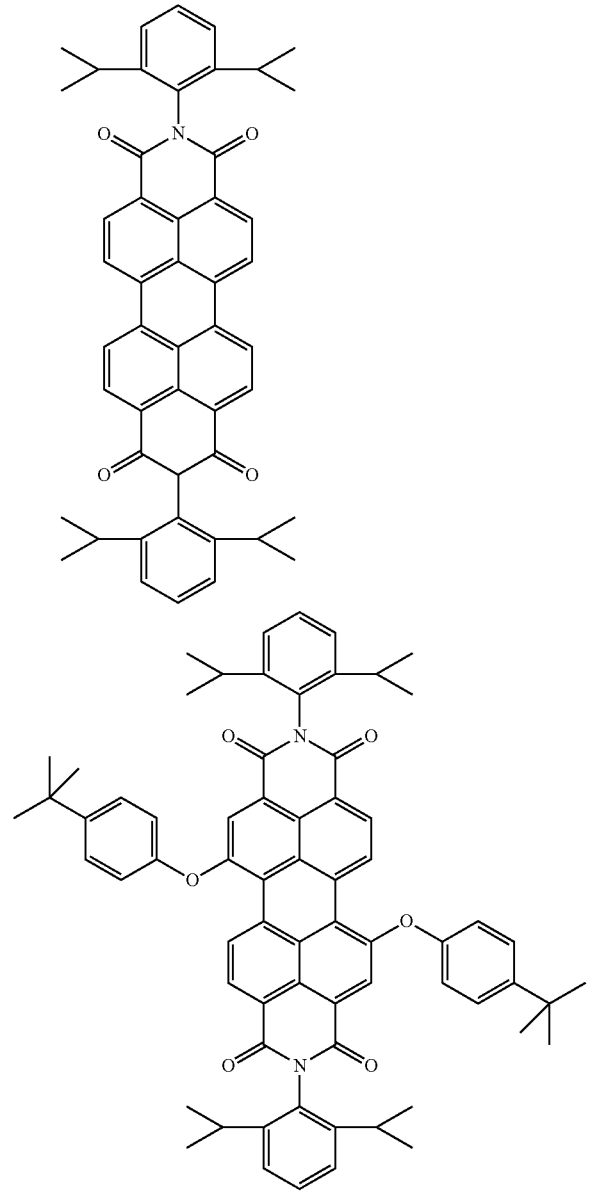

-continued

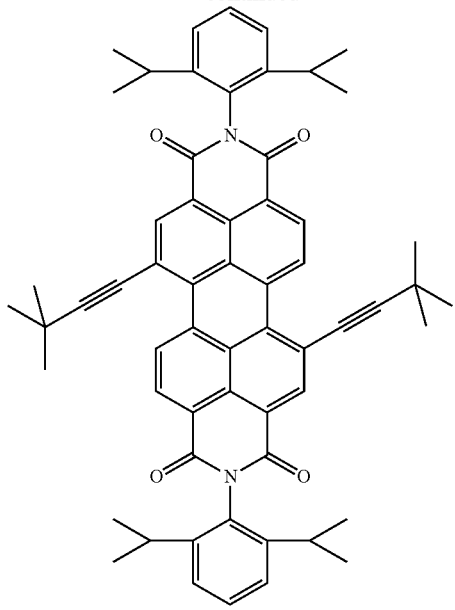

(XXI)

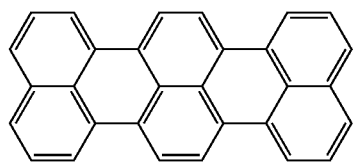

wherein

R and R1 to R15 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XXI), in which one to four of R and R1 to R15 are independently from each other aralkyl, aralkenyl, aralkinyl or aryl, whereas the remaining of R and R1 to R15 are hydrogen or $C_{1-10}$-alkyl, More preferably, in the general formula (XXI) one to four of R and R1 to R15 are independently from each other aralkyl, aralkenyl, aralkinyl or aryl, whereas the remaining of R and R1 to R15 are hydrogen.

Exemplarily, notably good results are obtained, when the composition in accordance with the present invention contains as emissive compound at least one polycyclic hydrocarbon compound according to the following formula:

According to still an alternative embodiment, the composition in accordance with the present invention contains as the emissive compound at least one polycyclic hydrocarbon according to the general formula (XXI):

According to still an alternative embodiment, the composition in accordance with the present invention contains as the emissive compound at least one polycyclic hydrocarbon according to the general formula (XXII):

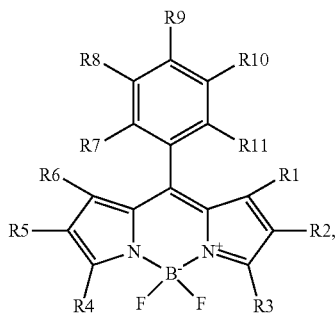

(XXII)

wherein

R1 to R11 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains.

Even better results are obtained, when the composition in accordance with the present invention includes as the at least one polycyclic hydrocarbon compound a compound according to the general formula (XXII), in which one to four of R and R1 to R11 are independently from each other aralkyl, aralkenyl, aralkinyl, aryl or hydroxyaryl, whereas the remaining of R and R1 to R11 are hydrogen or $C_{1-10}$-alkyl. More preferably, in the general formula (XXII) one to four of R and R1 to R11 are independently from each other aryl or hydroxyaryl, whereas the remaining of R and R1 to R11 are hydrogen. Even more preferably, in the general formula (XXII) one to four of R and R1 to R11 are independently from each other phenyl or hydroxyphenyl, whereas the remaining of R and R1 to R11 are hydrogen.

Exemplarily, notably good results are obtained, when the composition in accordance with the present invention contains as emissive compound at least one polycyclic hydrocarbon compound according to any of the following formulae:

5a

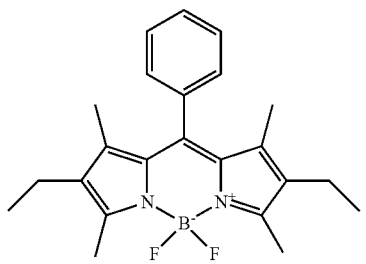

5b

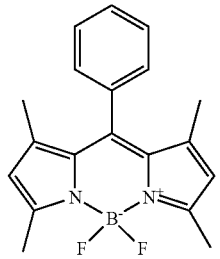

5c

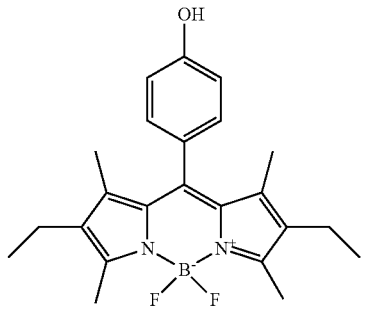

5d

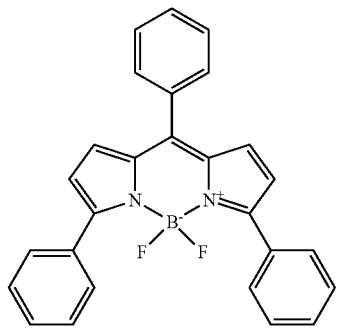

According to a further embodiment of the present invention, the composition comprises as at least one compound, which has a triplet state capable of energy transfer via an emissive process or a non-emissive process, and preferably as sensitizer compound at least one substituted or unsubstituted porphyrin compound.

Preferably, the composition in accordance with the present invention contains at least one porphyrin compound according to the general formula (XXIII):

(XXIII)

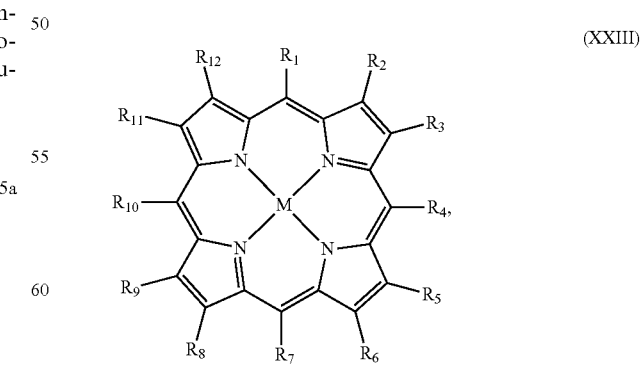

wherein
R1 to R12 are independently from each other selected from the group consisting of H, alkyl, alkenyl, alkynyl, aralkyl, aralkenyl, aralkinyl, aryl, carboxy, alkoxy, alkylthio, aryloxy, arylthio, alkoxycarbonyl, aryloxycarbonyl, alkylcarbonyl, arylcarbonyl, amino, alkylamino, arylamino, amide with alkyl or aryl groups, sulfonyl, alkylsulfonyl, arylsulfonyl and arbitrary combination of two or more of these groups, wherein all of these can be substituted with linear or branched alkyl groups, negatively charged groups, such as sulfate or carboxyl, positively charged groups, such as an ammonium group, neutral groups, such as polyethylene glycol or polyvinyl alcohol chains, and wherein any pair of two adjacent R1 to R12 may form a substituted or unsubstituted cyclohexyl, phenyl, naphthyl, anthracenyl group and, wherein M is selected from the group consisting of zinc, copper, nickel, magnesium, iron, cadmium, tin, lead, palladium, platinum, ruthenium, rhenium, iridium, osmium, gold, bismuth and uranium, wherein each of these metals can carry additional ligands.

All of these metals can may carry one or more additional ligand(s), such as chloride, bromide, oxygen, amine(s), phosphine(s), heterocyclic aromatic hydrocarbon(s) and/or β-diketones.

Each of these compounds can be substituted with linear or branched alkyl groups for better solubility in organic solvents, with negatively charged groups for water solubility, such as sulfate or carboxyl, with positively charged groups for water solubility, such as ammonium, and/or with neutral water-solubilizing groups, such as polyethylene glycol or polyvinyl alcohol chains.

According to a further preferred embodiment of the present invention, the at least one porphyrin compound is a compound according to the general formula (XXIII), wherein M is palladium, platinum, ruthenium or copper.

Notably good results are obtained, when the at least one porphyrin compound is a compound according to the general formula (XXIII), wherein each of R1, R4, R7 and R10 are independently from each other aryl, alkyl, aralkyl, aralkenyl or aralkynyl and preferably phenyl, naphthyl, anthracenyl or phenylethynyl, whereas the remaining residues are hydrogen.

Exemplarily, in this embodiment the at least one porphyrin compound may be a compound according to any of the subsequent general formulae:

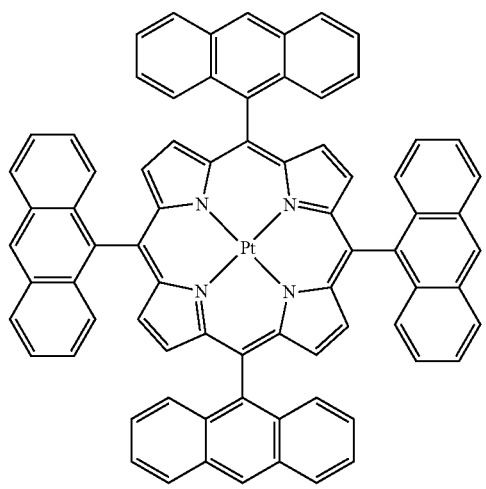

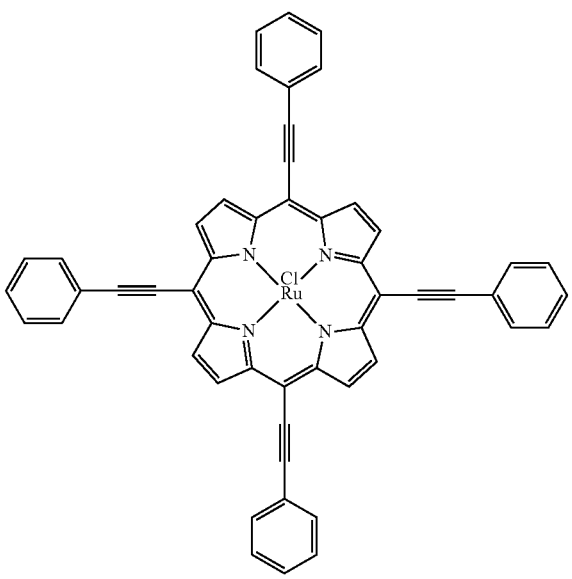

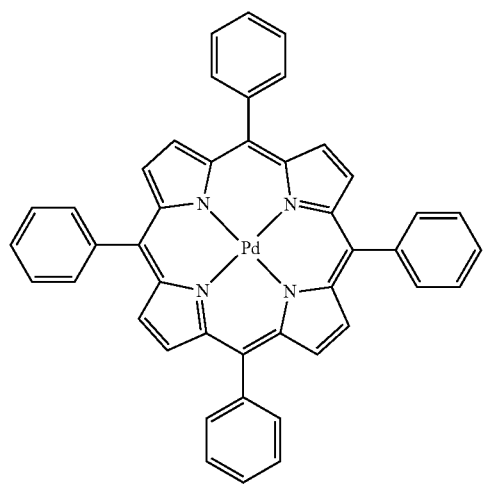

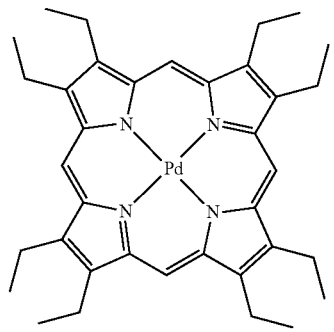

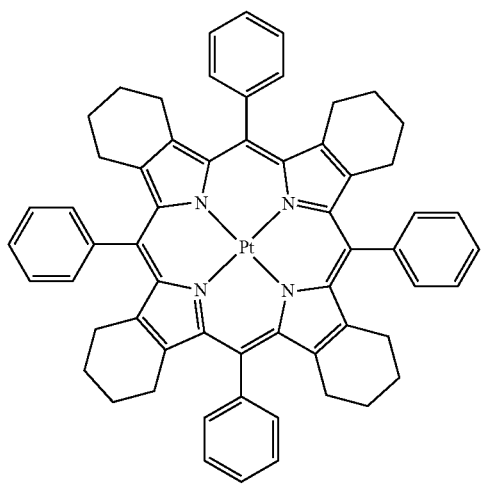

According to a further preferred embodiment of the present invention, the composition contains as the at least one porphyrin compound a substituted or unsubstituted mono-, di-, tri- or tetraphenylporphyrin according to any of the subsequent general formulae (XXIV) to (XXVIII):

(XXIV)

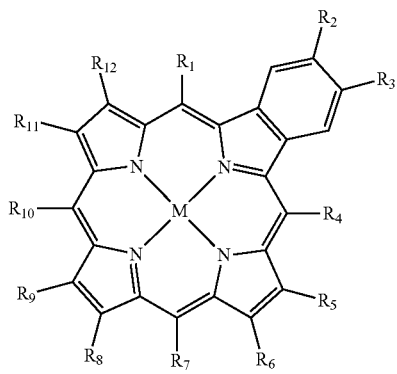

(XXV)

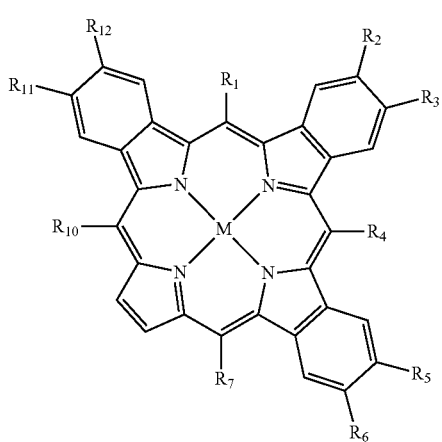

(XXVI)

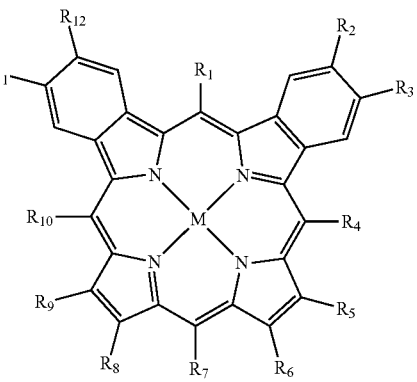

(XXVII)

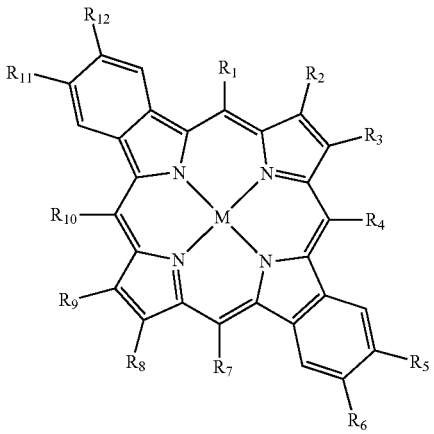

(XXVIII)

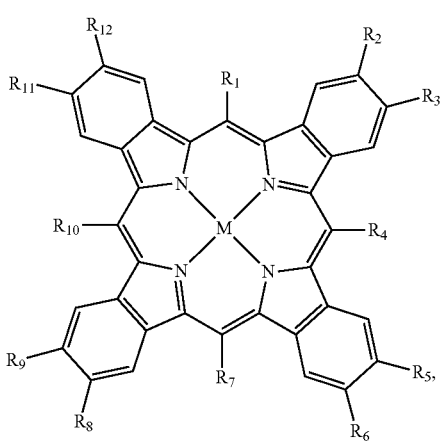

wherein

M and R1 to R12 are independently from each other as defined above for the general formula (XXIII).

Exemplarily, the composition may contain as the at least one porphyrin compound a compound according to any of the subsequent formulae:

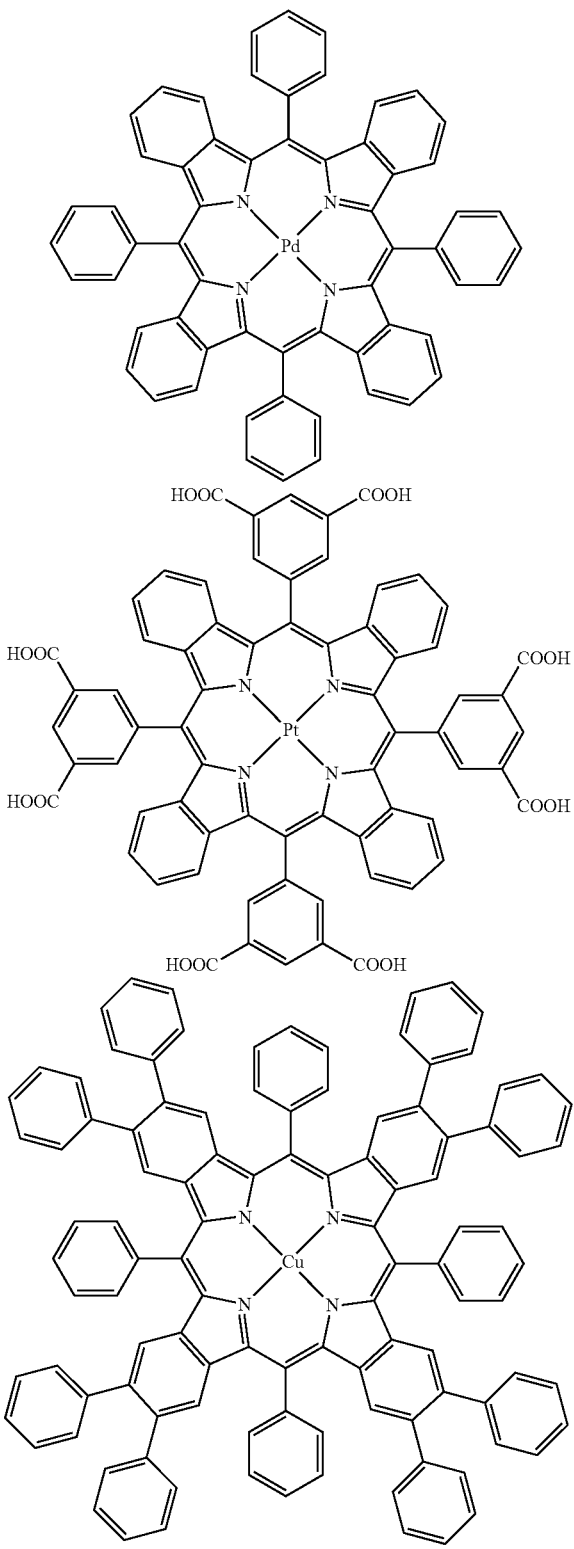
(XXIX)
(XXX)
(XXXI)
According to still a further preferred embodiment of the present invention, the composition contains as the at least one porphyrin compound a substituted or unsubstituted mono-, di-, tri- or tetranaphthyl[2,3]porphyrin according to any of the subsequent general formulae (XXIX) to (XXXIII):

-continued (XXXII)

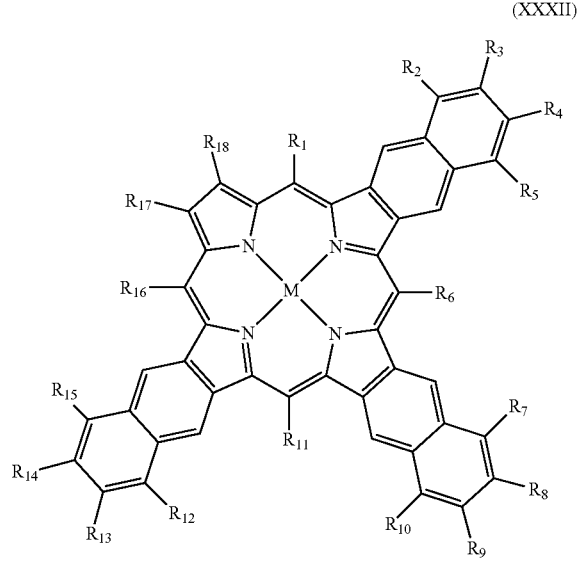

(XXXIII)

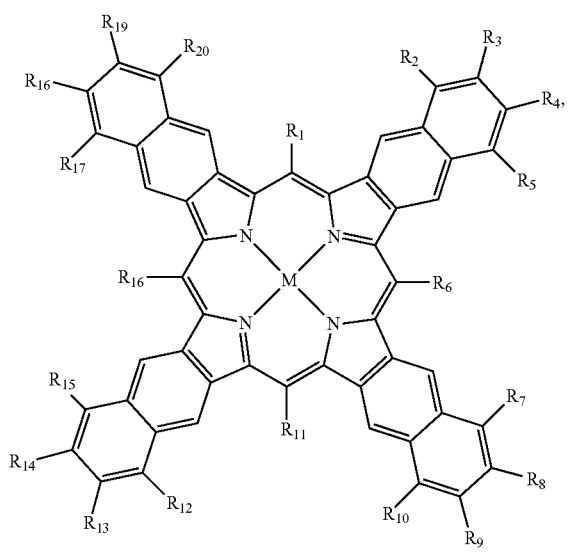

wherein
M and R1 to R20 are independently from each other as defined above for residues R1 to R12 of the general formula (XXIII).

Preferably, the at least one porphyrin compound is a compound according to any of the subsequent formulae:

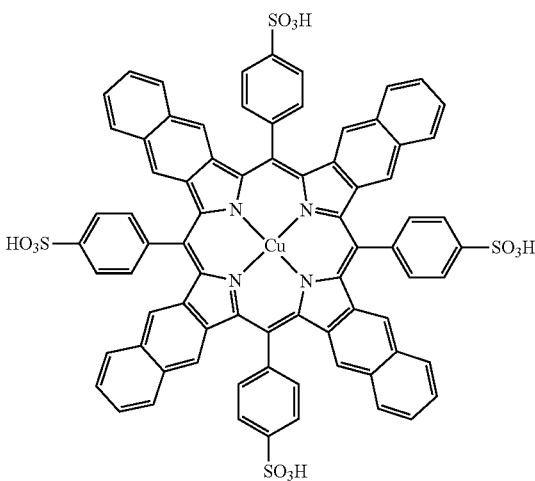

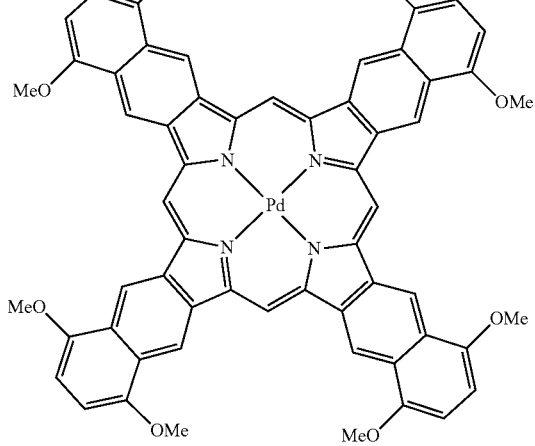

According to still a further preferred embodiment of the present invention, the composition contains as the at least one porphyrin compound a substituted or unsubstituted mono-, di-, tri- or tetranaphthyl[1,2]porphyrin according to any of the subsequent general formulae (XXXIV) to (XXXVIII):

(XXXIV)

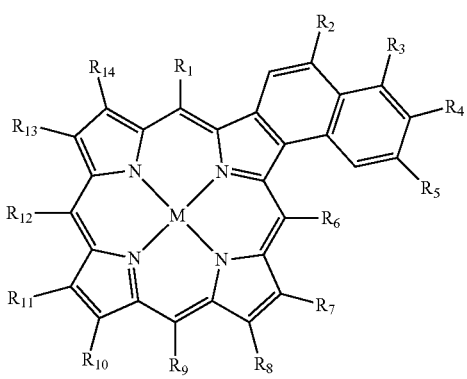

(XXXV)

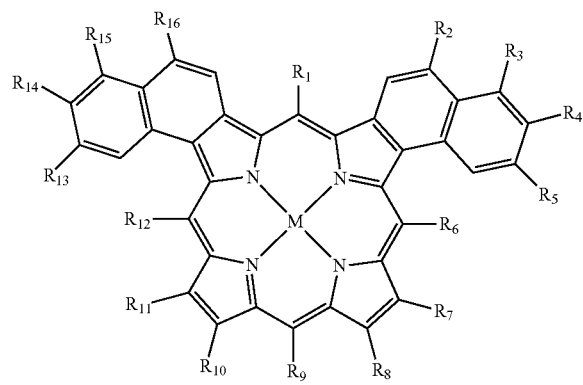

(XXXVI)

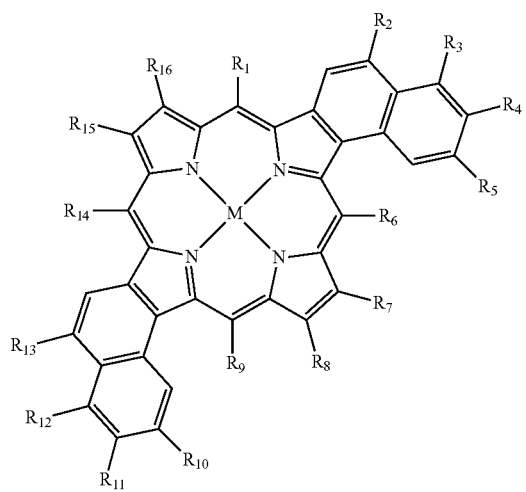

(XXXVII)

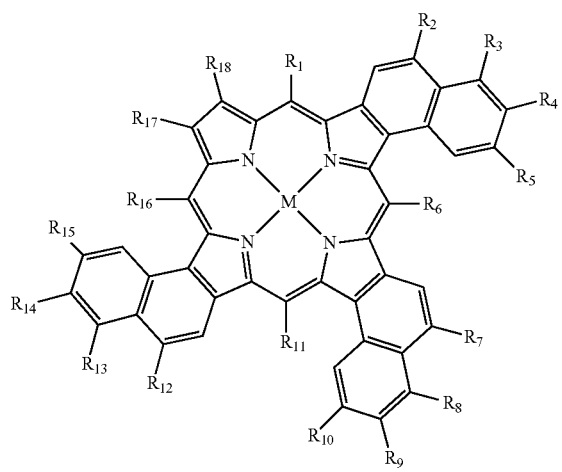

(XXXVIII)

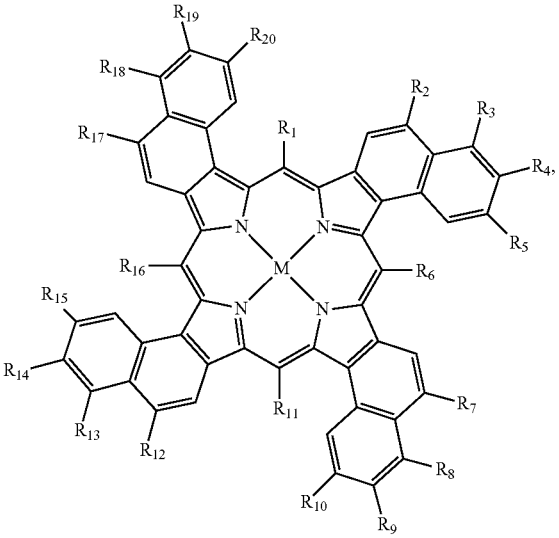

wherein
M and R1 to R20 are independently from each other as defined above for residues R1 to R12 of the general formula (XXIII).

Preferably, the at least one porphyrin compound is a compound according to any of the subsequent formulae:

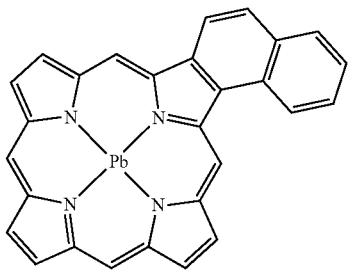

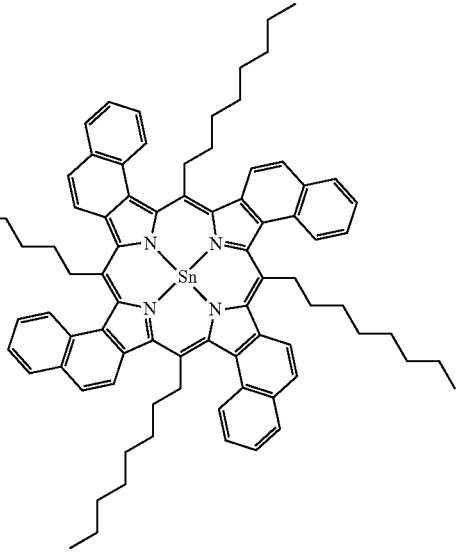

According to still a further preferred embodiment of the present invention, the composition contains as the at least one porphyrin compound a substituted or unsubstituted mono-, di-, tri- or tetraanthracenylporphyrin according to any of the subsequent general formulae (XXXIX) to (XXXXIII):
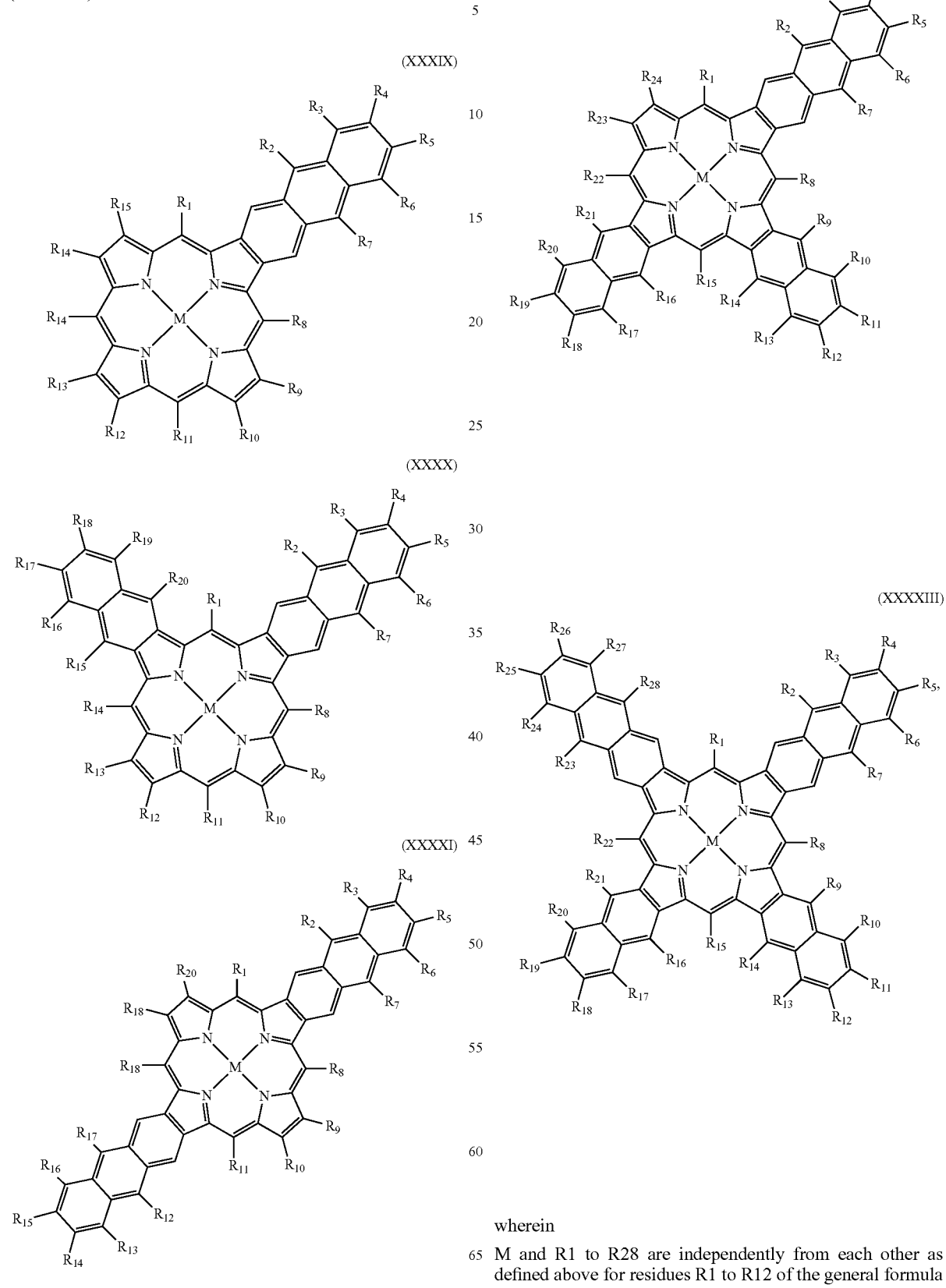
(XXXIX)
(XXXX)
(XXXXI)
(XXXXII)
(XXXXIII)
wherein
M and R1 to R28 are independently from each other as defined above for residues R1 to R12 of the general formula (XXIII).

Preferably, the at least one porphyrin compound is a compound according to any of the subsequent formulae:
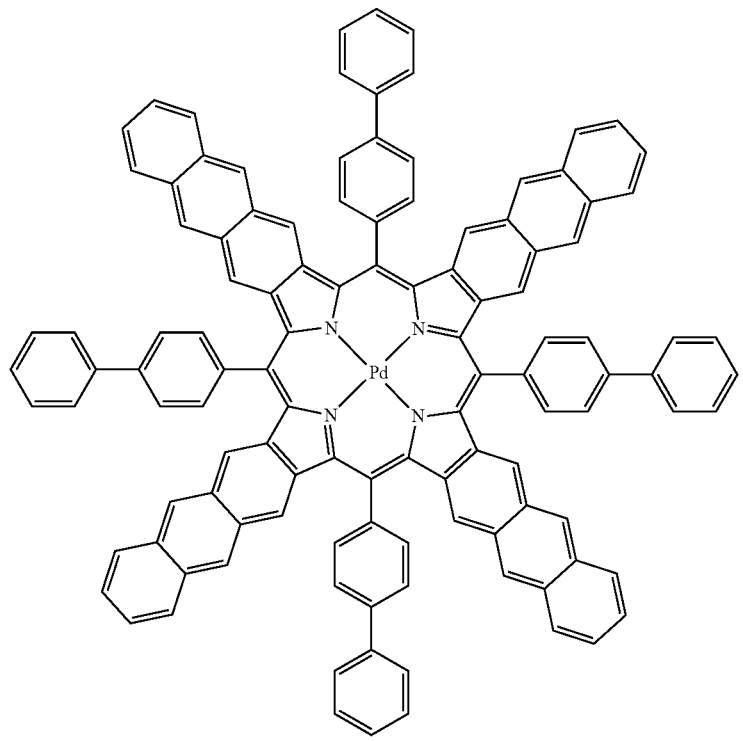
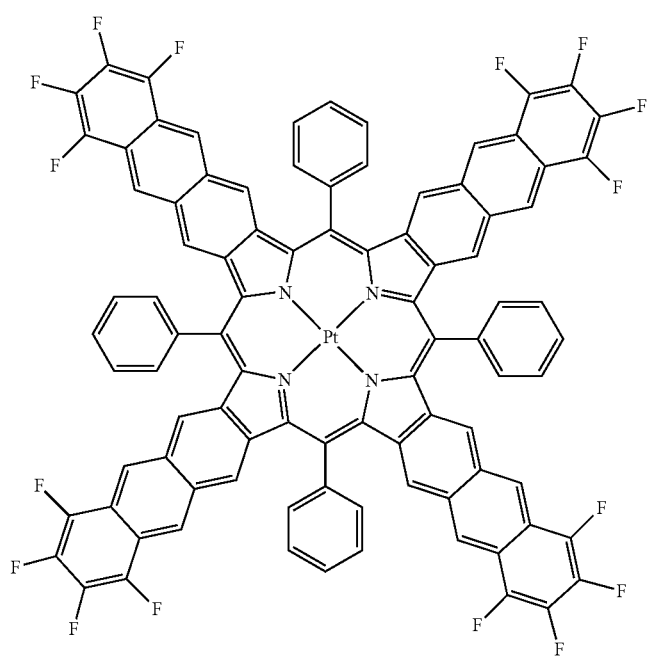

According to still a further preferred embodiment of the present invention, the composition contains as the at least one porphyrin compound a substituted or unsubstituted mono-, di-, tri- or tetraarylporphyrin according to any of the subsequent general formulae (XXXXIV) to (LI):
(XXXXIV)
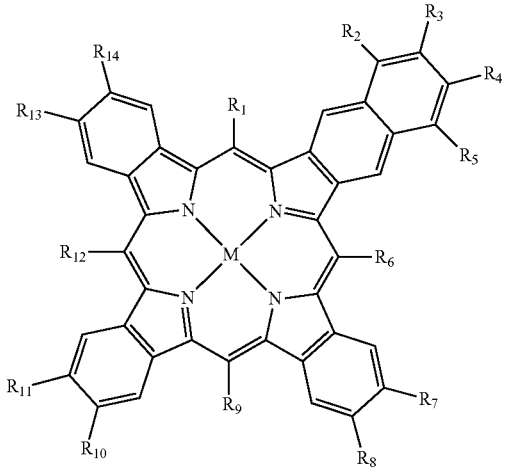
(XXXXV)
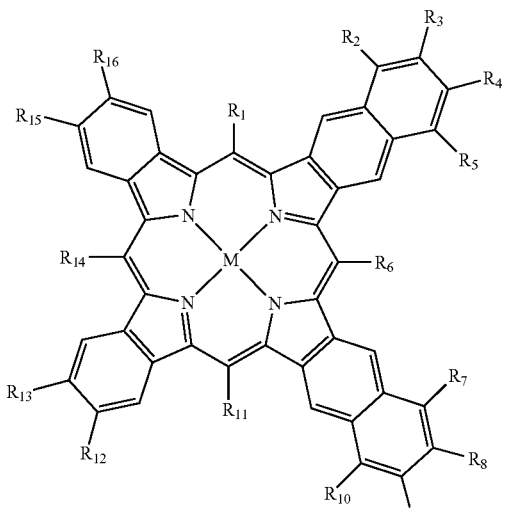
(XXXXVI)
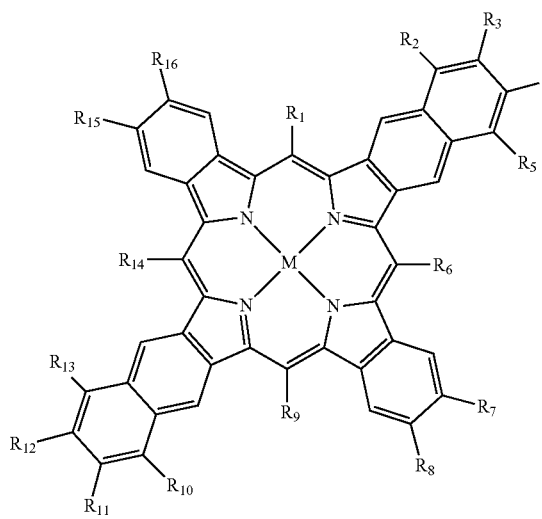
(XXXXVII)
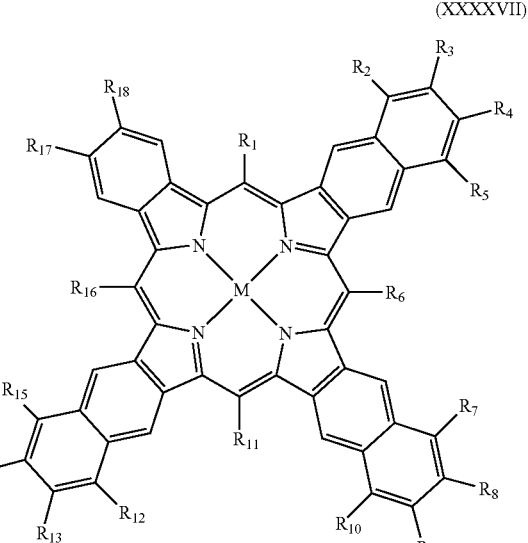
(XXXXVIII)
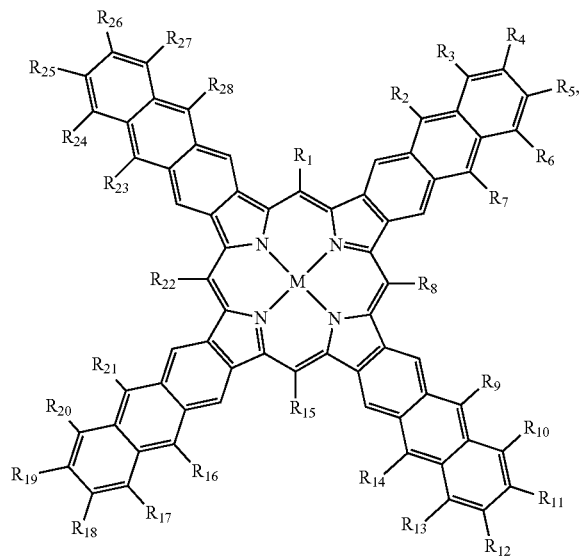
(XXXXIX)
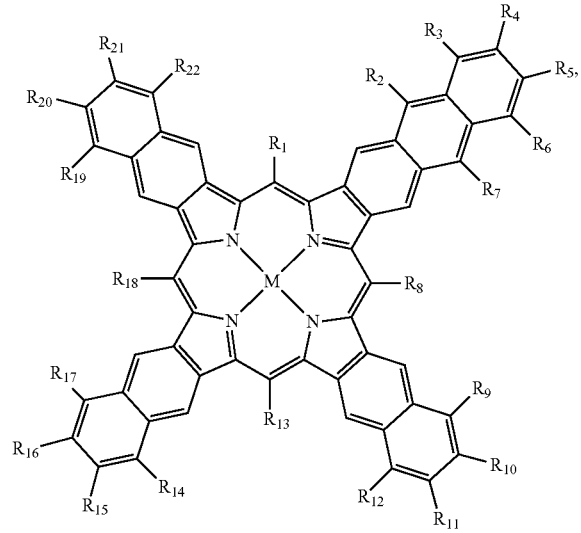

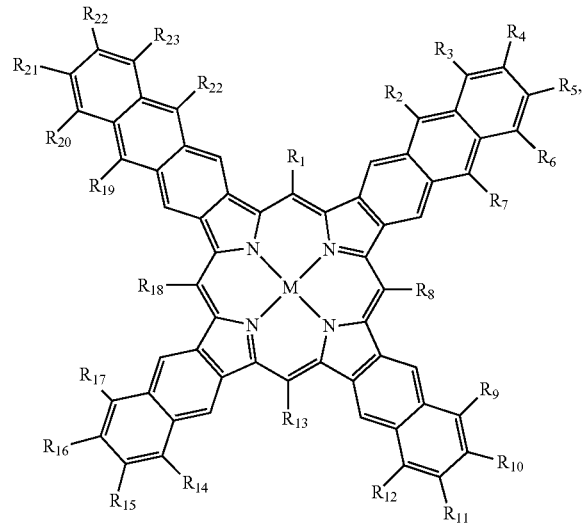

(L)

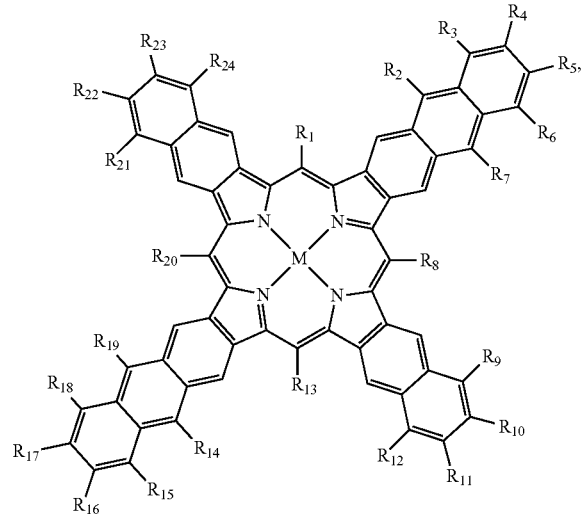

(LI)

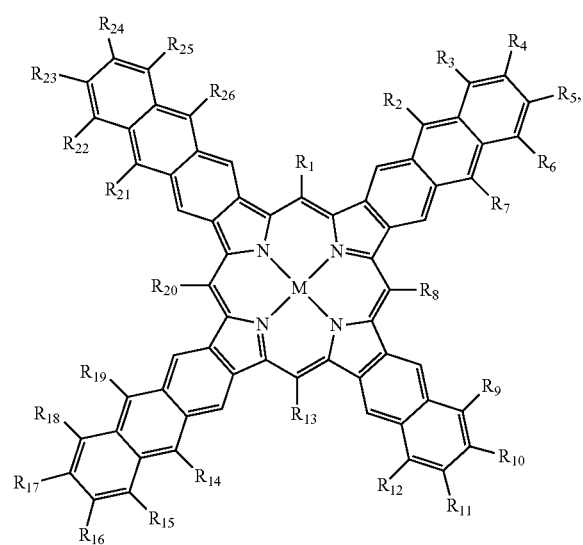

(LII)

wherein

M and R1 to R26 are independently from each other as defined above for residues R1 to R12 of the general formula (XXIII), Preferably, the at least one porphyrin compound is a compound according to any of the subsequent formulae:

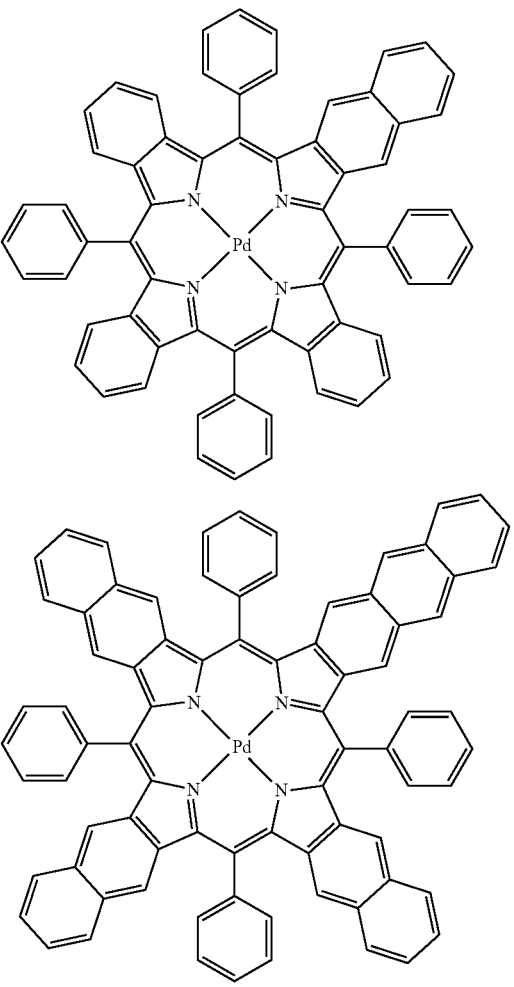

In an alternative embodiment, the sensitizer is an aromatic hydrocarbon, which is substituted with at least one heavy atom, such as a halogen, such as Br, Cl and/or I. Suitable examples for such compounds are:

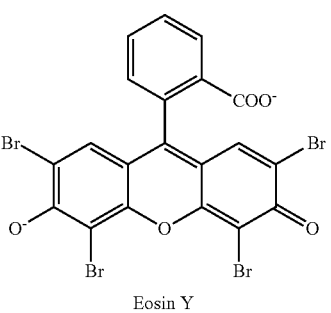

Eosin Y

-continued

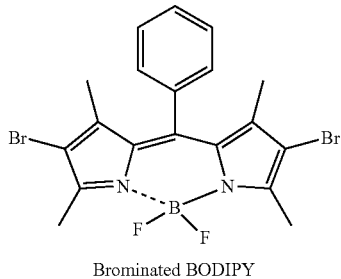

Brominated BODIPY and

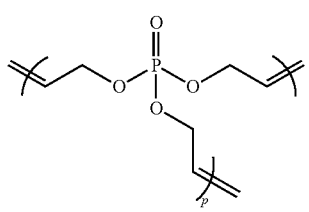

iodinated BODIPY

Moreover, the present invention relates to polyphosphoesters according to the general formula (Xa):

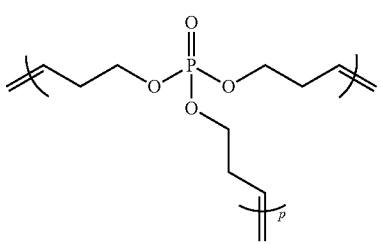

(Xa)

wherein
n, m and o are independently from each other an integer between 1 and and
p is an integer of 2 or more and preferably an integer of 2 to 120.

Preferably, the polyphosphoester is a compound according to the general formula (Xa), wherein n, m and o are independently from each other an integer between 2 and 11 and p is an integer of 2 to 120. Even more preferably, the polyphosphoester is a compound according to the general formula (Xa), wherein n, m and o are independently from each other an integer between 4 and 11 and p is an integer of 3 to 40.

Furthermore, the hyperbranched phosphoester compound according to the formula (Xa) has preferably a total number of terminal unsaturated carbon-carbon bonds per molecule of 4 or more, more preferably between 4 and 122 and even more preferably between 5 and 42.

More preferably, the polyphosphoester is a compound according to any of the subsequent formulae (XI) to (XIV):

(XI)

(XII)

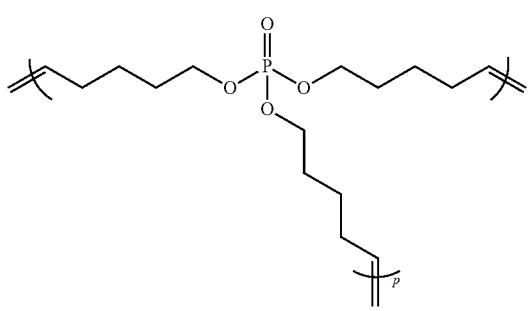

(XIII)

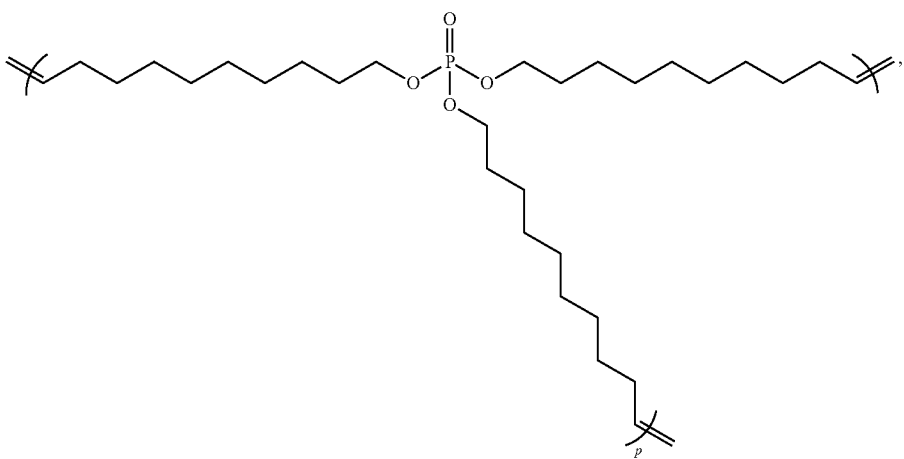

(XIV)

wherein in each of the formulae p is an integer of 2 to 120 and preferably p is an integer of 3 to 40.

Even more preferably, the polyphosphoester has a number average molecular weight determined by gel permeation chromatography of 500 to 50,000 g/mol.

Subsequently, the present invention will be described in more detail by way of non-limiting examples and comparative examples making reference to the figures, wherein:

FIG. 1 is a luminescence spectrum comparing a composition including MF16 (example 1) as singlet oxygen inhibitor with a composition including toluene (comparative example 1) as solvent.

FIG. 2 shows the dependency of the integral UC-fluorescence on the excitation intensity for the compositions of examples 1 and 2 and of comparative example 1.

FIG. 3 is a luminescence spectrum comparing a composition including MF81 (example 2) as singlet oxygen inhibitor with a composition including MF16 (example 1) as solvent.

FIG. 4 is a luminescence spectrum comparing a composition including MF54 (example 5), MF82 (example 6) and MF14 (example 7) as singlet oxygen inhibitor.

EXAMPLE 1 AND COMPARATIVE EXAMPLE 1

(Singlet Oxygen Protection at TTA-UC by an Organophosphate Monomer)

Di-(5-hexen-1-yl) phenyl phosphate (subsequently abbreviated as MF16) was used as singlet oxygen inhibitor in a composition in accordance with the present invention. More specifically, a composition consisting of $1 \cdot 10^{-4}$ mol/l 2,7,8,12,13,17,18-octaethylporphyrin platinum (PtOEP) as sensitizer compound, $2 \cdot 10^{-3}$ mol/l 1,2,3,4-dibenzanthracene (perylene) as emissive compound and MF16 as singlet oxygen inhibitor was prepared.

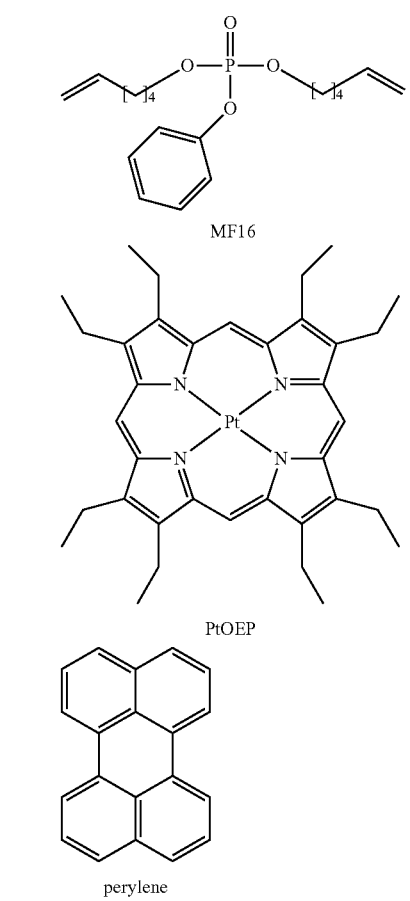

MF16

PtOEP perylene

Afterwards, the composition was shaped to a cuboid having a thickness of 400 μm. Then, a luminescence spectrum of the sample was recorded at room temperature using an excitation wavelength of 532 nm and an excitation laser intensity of 3.17 W/cm² at glove box atmosphere having an oxygen concentration of 2 ppm.

For comparison, a composition according to comparative example 1 was prepared as described above for example 1 except of using toluene instead of MF16. A luminescence spectrum of this sample was recorded under the same conditions described above for example 1. The results are shown in FIG. 1.

Figure 1:
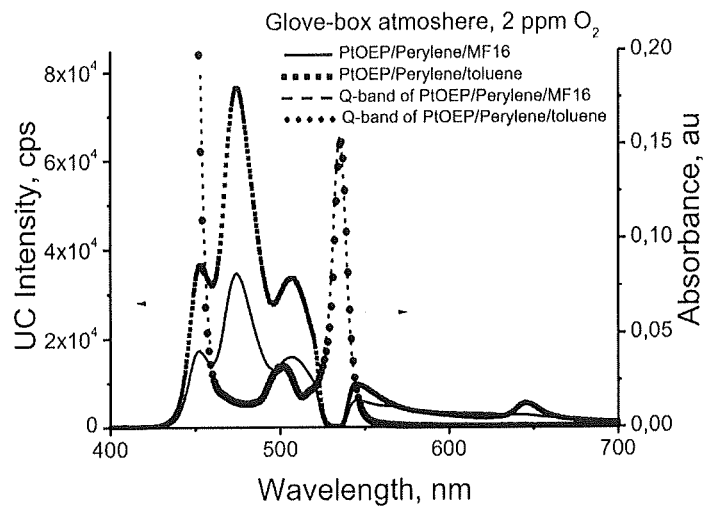

As it derives from FIG. 1, the TTA-UC efficiency of the composition of example 1 including MF16 as solvent is comparable with that of the composition of comparative example 1 including toluene, when glove-box atmosphere is used.

Figure 2:
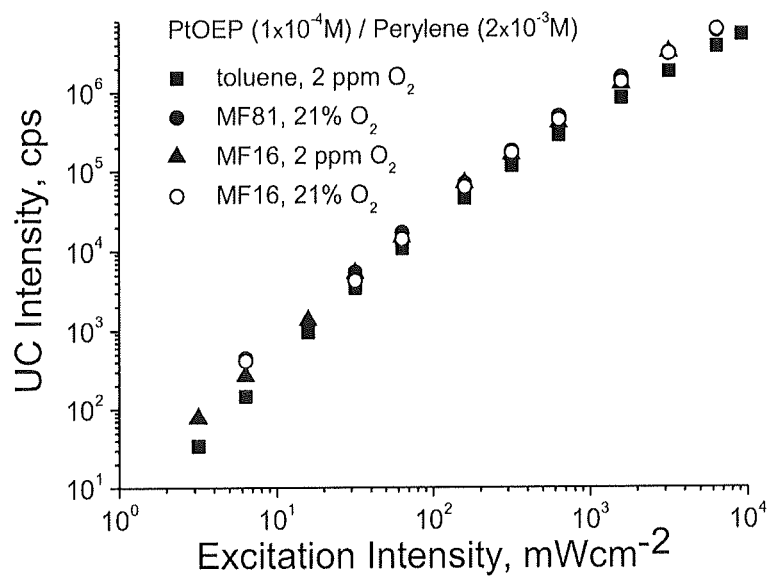

Moreover, for both compositions the TTA-UC-fluorescence has been measured in dependency of the excitation intensity in different atmospheres having different oxygen concentrations. The results are shown in FIG. 2. As it derives from FIG. 2, the TTA-UC efficiencies for the composition of example 1 are nearly identical at 2 ppm oxygen concentration and at 21% oxygen concentration and are higher than that of the composition of comparative example 2 at glove-box conditions, i.e. in an atmosphere with 2 ppm oxygen concentration.

EXAMPLE 2

(Singlet Oxygen Protection at TTA-UC by an Organophosphate Monomer)

Example 1 was repeated except of using as singlet oxygen inhibitor tri-(5-hexen-1-yl) phosphate (MF81) instead of MF16.

MF81

The composition of example 2 was evaluated as described above for the composition of example 1 in comparison to that of the comparative example 1 except that the luminescence spectrum was recorded in ambient atmosphere with an oxygen concentration of 21%.

Figure 3:
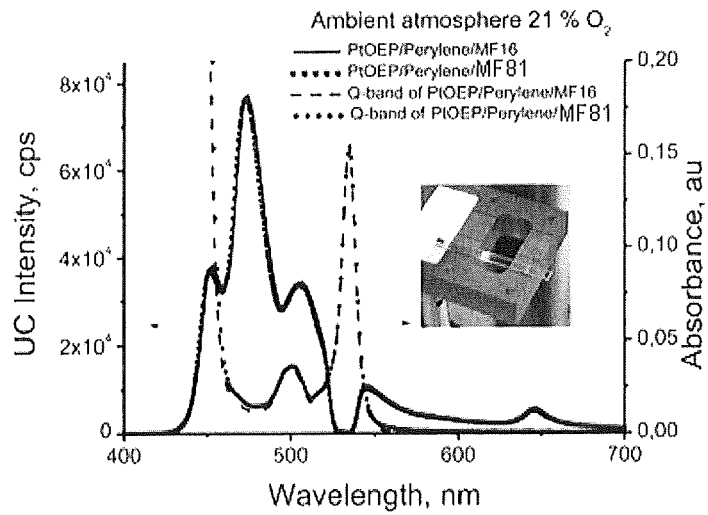

The results are shown in FIGS. 2 and 3.

As it derives from FIG. 3, the TTA-UC efficiency of the composition of example 2 including MF81 as solvent is as high as for MF16 (example 1) and thus much higher than that of the composition of comparative example 1 including toluene. Moreover, the TTA-UC efficiencies for the composition of example 2 are nearly identical at 2 ppm oxygen concentration and at 21% oxygen concentration and are higher than that of the composition of comparative example 2 at glove-box atmosphere, i.e. at 2 ppm oxygen concentration.

EXAMPLES 3 AND 4

(Singlet Oxygen Protection at TTA-UC by an Organophosphate Monomer)

Example 2 was repeated except that as sensitizer and emissive compounds PdTBP and Y805 for example 3 and PdTNP and Y808 for example 4 were used.

PdTBP

Y805

PdTNP

-continued

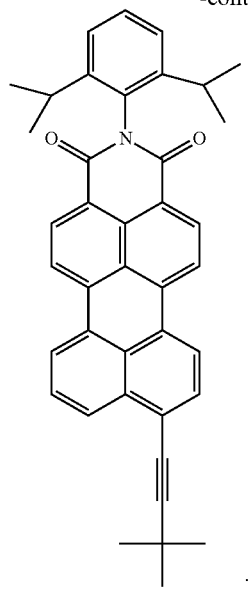

Y808

A luminescence spectrum of the samples were recorded at room temperature using an excitation wavelength of 532 nm and an excitation laser intensity of 3.17 W/cm² in atmospheres having oxygen concentrations of 2 ppm and 21% for example 3 and in an atmospheres having an oxygen concentration of 21% for example 4.

Similar good results were obtained as for examples 1 and 2. This shows that the advantageous properties of the composition in accordance with the present patent application are due to the addition of the singlet oxygen inhibitor comprising at least one terminal unsaturated carbon-carbon bond and are achieved for different sensitizer and emissive compounds.

EXAMPLES 5 TO 7

(Singlet Oxygen Protection at TTA-UC by Hyperbranched Polyphosphoesters)

Example 1 was repeated except that three different hyperbranched polyphosphoesters according to the following formulae were used as singlet oxygen inhibitor:

MF54

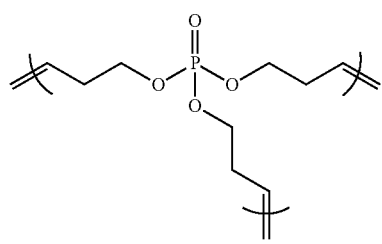

MF82

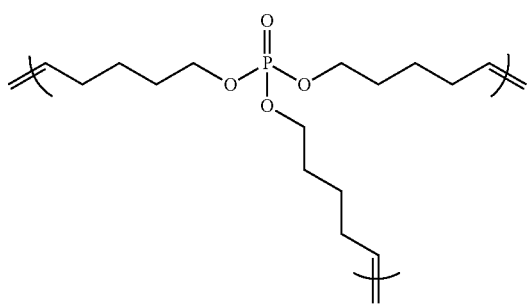

MF14

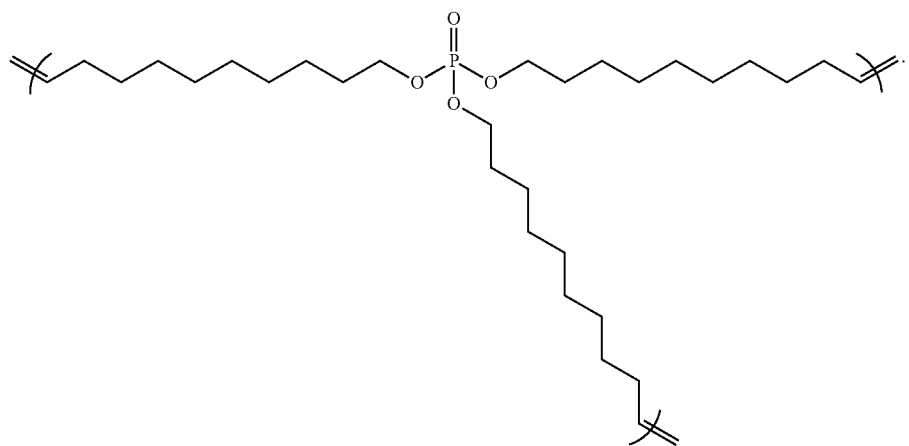

Figure 4:
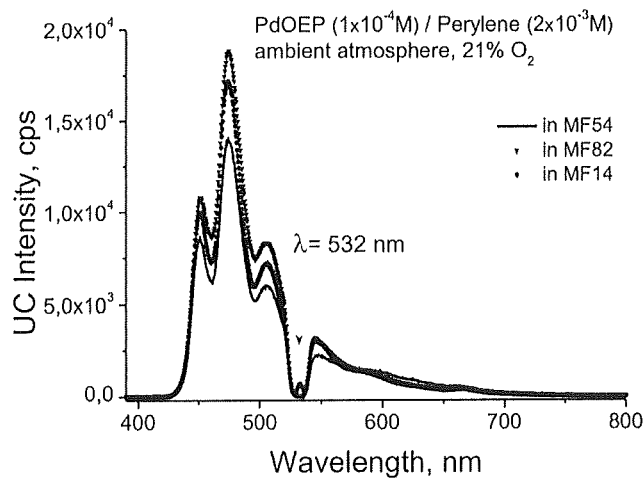

A luminescence spectrum of the samples were recorded at room temperature using an excitation wavelength of 532 nm and an excitation laser intensity of 3.17 W/cm$^2$ in ambient atmosphere having an oxygen concentration of 21%. The results are shown in FIG. 4. Similar good results were obtained as for examples 1 to 4.

EXAMPLES 8 AND 9

(Singlet Oxygen Protection at TTA-UC by Alcohol and Silicate)

Example 1 was repeated except that the following two compounds were used as singlet oxygen inhibitor:

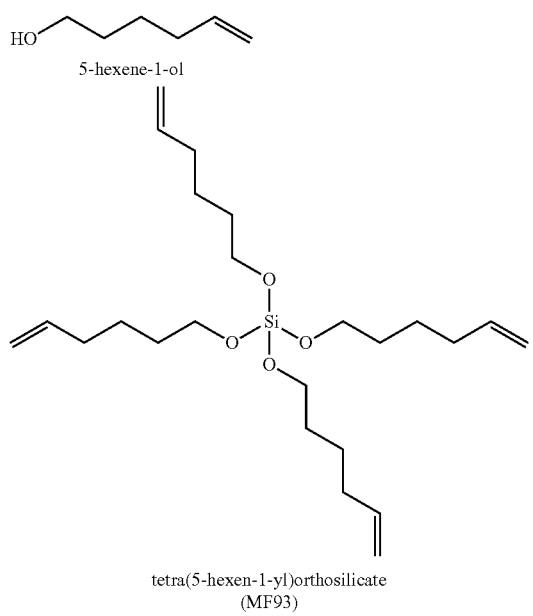

5-hexene-1-ol tetra(5-hexen-1-yl)orthosilicate
(MF93)

A luminescence spectrum of the samples were recorded at room temperature using an excitation wavelength of 532 nm and an excitation laser intensity of 3.17 W/cm$^2$ in atmospheres having oxygen concentrations of 2 ppm and of 21%. Similar good results were obtained as for examples 1 to 7.

EXAMPLE 10 AND COMPARATIVE EXAMPLE 2

(Singlet Oxygen Protection at Phosphorescence by an Organophosphate Monomer)

A phosphorescent composition consisting of $1 \cdot 10^{-4}$ mol/l PtOEP as sensitizer/phosphorescent compound and MF16 as singlet oxygen inhibitor was prepared (example 10).

Afterwards, the composition was shaped to a cuboid having a thickness of 400 μm. Then, a phosphorescence spectrum of the sample was recorded at room temperature using an excitation wavelength of 532 nm at different excitation laser intensities in ambient atmosphere with an oxygen content of 21%.

For comparison, a composition according to comparative example 2 was prepared as described above for example 10 except of using toluene instead of MF16. Phosphorescence spectra of this sample were recorded under the conditions described above for example 10. The results are shown in FIGS. 5 and 6.

Figure 5:
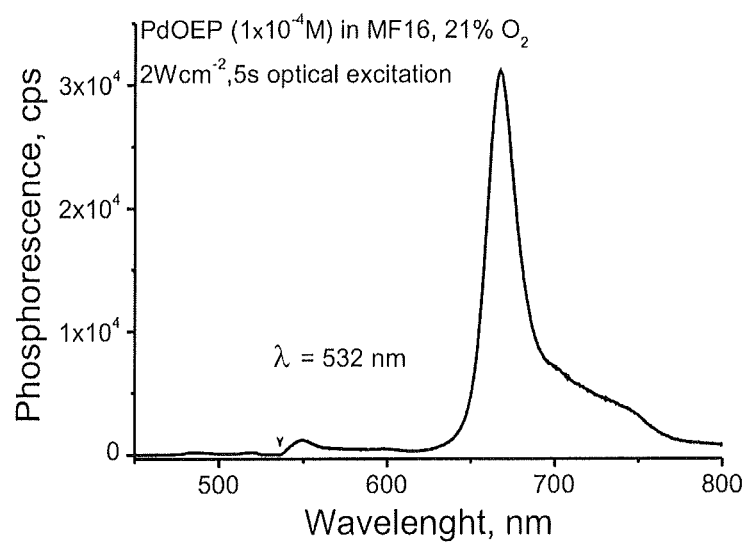
FIG. 5 is a phosphorescence spectrum of a composition including MF16 (example 10).
Figure 6:
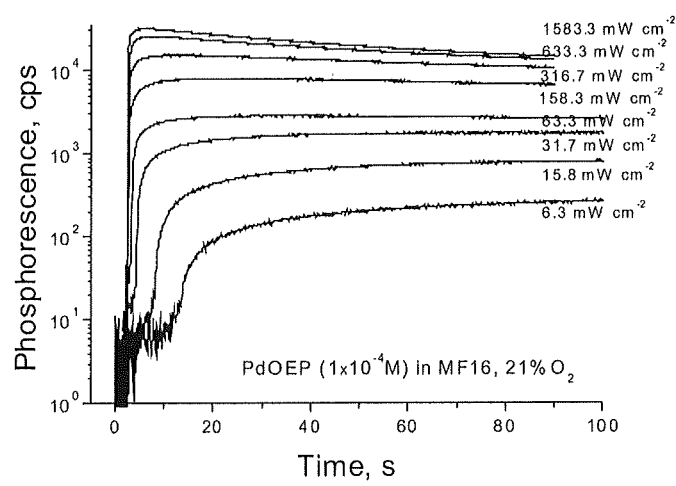
FIG. 6 are phosphorescence spectra for a composition including MF16 (example 10) as singlet oxygen inhibitor at different excitation laser intensities.

As it derives from FIGS. 5 and 6, the process of phosphorescence of metallated macrocycles is effectively protected for long temporal period from quenching by oxygen independent from the excitation laser intensity, when using at least one compound capable of reacting with singlet oxygen comprises at least one terminal unsaturated carbon-carbon bond.

EXAMPLE 11

(Determination of Number of Terminal Carbon-Carbon Double Bonds in a Hyperbranched Phosphoester)

The following hyperbranched phosphoester was prepared.

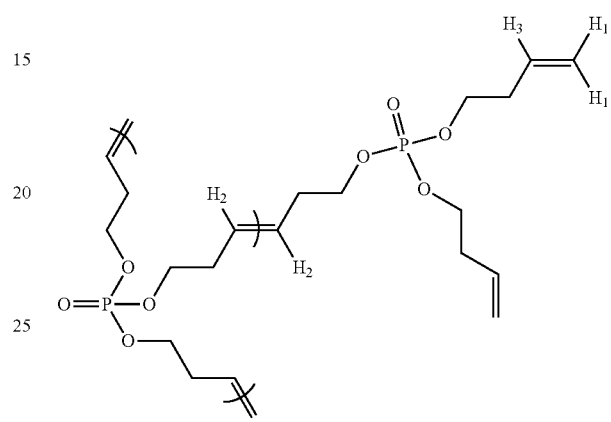

Figure 7:
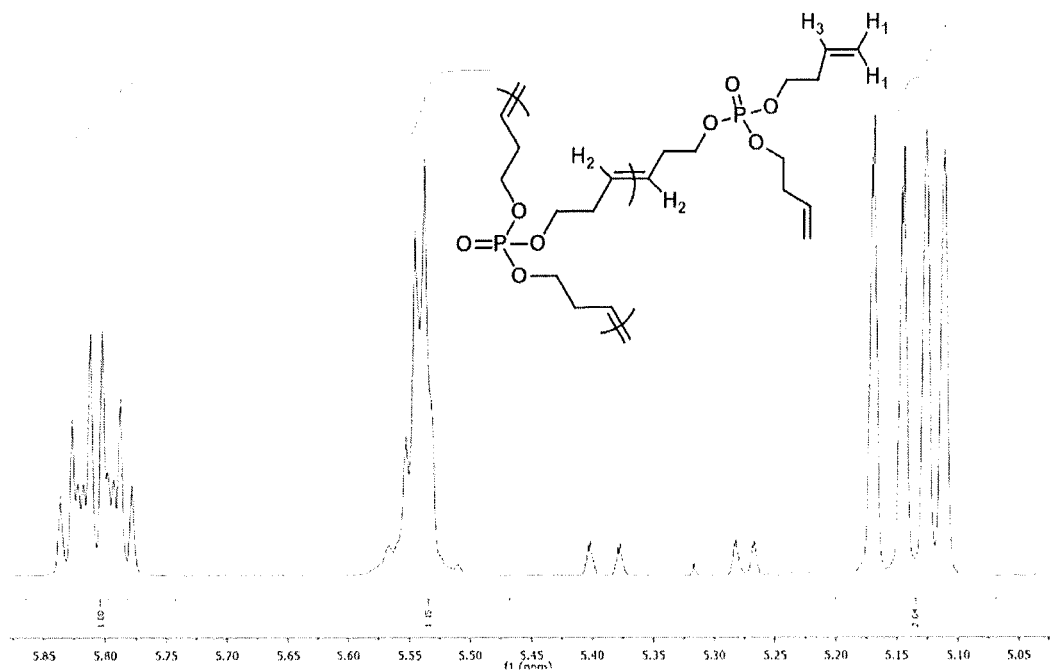
FIG. 7 is the $^1$H-NMR spectrum of the hyperbranched phosphoester of example 11.

Afterwards, the number average molecular weight of the phosphoester was determined with GPC as described above as being 4,500 g/mol. Moreover, it was confirmed by SEC analysis that no monomers were present in the system. Then, a $^1$H-NMR spectrum was recorded, which is shown in FIG. 7. In this spectrum, the ratio of the signal intensities for terminal and the internal double bonds was 1:1.

It follows from these results that the polymer has a polymerization degree of 20 and that it carries 20 terminal carbon-carbon double bonds.

The invention claimed is:
1. A composition containing:
 a) at least one compound capable of reacting with singlet oxygen, and
 b) at least one compound, which has a triplet state capable of energy transfer via an emissive process or a non-emissive process, wherein the at least one compound having a triplet state is
  i) at least one phosphorescent compound sufficiently soluble in the compound capable of reacting with singlet oxygen and/or
  ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is capable of a triplet-triplet energy transfer to the at least one emissive compound,
 wherein the at least one compound capable of reacting with singlet oxygen comprises at least one terminal unsaturated carbon-carbon bond and is selected from the group consisting of compounds having anyone of the following general formulae (I) to (X):

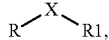
(I)

wherein
X is O or S,
R is alkenyl or alkynyl and
R1 is H, alkyl, ether-alkyl, ether-alkenyl, alkenyl, alkynyl, aralkyl, aryl or heteroaryl,

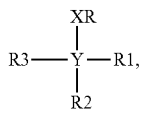
(II)

wherein
X is O or S,
R is alkenyl or alkynyl,
Y is alkyl, alkenyl, alkynyl, aralkyl, aralkenyl, aralkynyl, aryl or heteroaryl and
R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

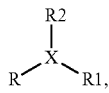
(III)

wherein
X is N or P,
R is alkenyl or alkynyl and
R1 and R2 are independently from each other H, alkyl, alkenyl, alkynyl, aralkyl, aryl or heteroaryl,

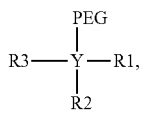
(IV)

wherein
PEG is an oligoethylene glycol or polyethylene glycol group having 2 to 99 ethylene glycol units,
R1 is alkenyl or alkynyl,
Y is Si and
R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

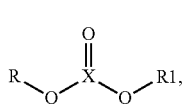
(V)

wherein
X is P, S, B or Si,
R is alkenyl or alkynyl and
R1 is H, alkyl, alkenyl, alkynyl, aralkyl, aryl or heteroaryl,

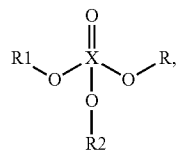
(VI)

wherein
X is P, S, B or Si,
R is alkenyl or alkynyl and
R1 and R2 are independently from each other H, alkyl, alkenyl, alkynyl, aralkyl, aryl or heteroaryl,

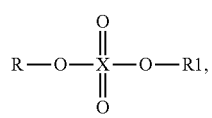
(VII)

wherein
X is P, S, B or Si,
R is alkenyl or alkynyl and
R1 is H, alkyl, alkenyl, alkynyl, aralkyl, aryl or heteroaryl,

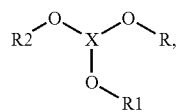
(VIII)

wherein
X is P, S, B or Si,
R is alkenyl or alkynyl and
R1 and R2 are independently from each other H, alkyl, alkenyl, alkynyl, aralkyl, aryl or heteroaryl,

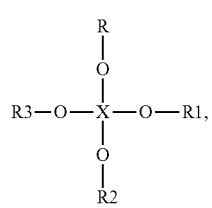
(IX)

wherein
X is P, S, B or Si,
R is alkenyl or alkynyl and
R1, R2 and R3 are independently from each other H, alkyl, alkenyl, alkynyl, aralkyl, aryl or heteroaryl,

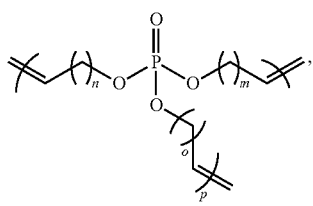 (Xa)

wherein
n, m and o are independently from each other an integer between 1 and 20 and
p is an integer of 2 or more,

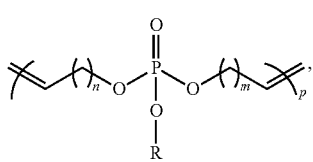 (Xb)

wherein
R is H, alkyl, alkenyl, alkynyl, aralkyl, aryl or heteroaryl,
n and m are independently from each other an integer between 1 and 20 and
p is an integer of 2 or more
or

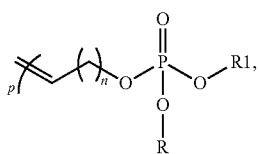 (Xc)

wherein
R and R1 are independently from each other H, alkyl, alkenyl, alkynyl, aralkyl, aryl or heteroaryl,
n is an integer between 1 and 20 and
p is an integer of 2 or more,
wherein the total concentration of all phosphorescent compounds is $1 \cdot 10^{-5}$ to $1 \cdot 10^{-3}$ mol/l, and wherein the total content of all phosphorescent compounds and all compounds comprising at least one terminal unsaturated carbon-carbon bond in the composition is at least 90 mol-%.

2. A composition containing:
a) at least one compound capable of reacting with singlet oxygen, and
b) at least one compound, which has a triplet state capable of energy transfer via an emissive process or a non-emissive process, wherein the at least one compound having a triplet state is
i) at least one phosphorescent compound sufficiently soluble in the compound capable of reacting with singlet oxygen and/or
ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is capable of a triplet-triplet energy transfer to the at least one emissive compound,
wherein the at least one compound capable of reacting with singlet oxygen comprises at least one terminal unsaturated carbon-carbon bond and is selected from the group consisting of compounds having anyone of the following general formulae (I) to (X):

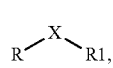 (I)

wherein
X is O or S,
R is alkenyl or alkynyl and
R1 is H, alkyl, ether-alkyl, ether-alkenyl, alkenyl, alkynyl, aralkyl, aryl or heteroaryl,

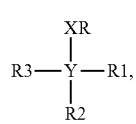 (II)

wherein
X is O or S,
R is alkenyl or alkynyl,
Y is alkyl, alkenyl, alkynyl, aralkyl, aralkenyl, aralkynyl, aryl or heteroaryl and
R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

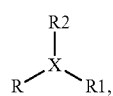 (III)

wherein
X is N or P,
R is alkenyl or alkynyl and
R1 and R2 are independently from each other H, alkyl, alkenyl, alkynyl, aralkyl, aryl or heteroaryl,

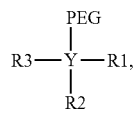 (IV)

wherein

PEG is an oligoethylene glycol or polyethylene glycol group having 2 to 99 ethylene glycol units, R1 is alkenyl or alkynyl, Y is Si and R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

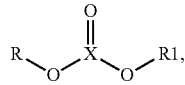
(V)

wherein

X is P, S, B or Si,

R is alkenyl or alkynyl and

R1 is H, alkyl, alkenyl, alkynyl, aralkyl, aryl or heteroaryl,

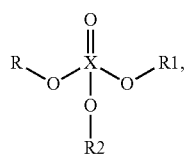
(VI)

wherein

X is P, S, B or Si,

R is alkenyl or alkynyl and

R1 and R2 are independently from each other H, alkyl, alkenyl, alkynyl, aralkyl, aryl or heteroaryl,

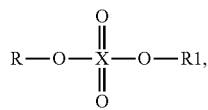
(VII)

wherein

X is P, S, B or Si,

R is alkenyl or alkynyl and

R1 is H, alkyl, alkenyl, alkynyl, aralkyl, aryl or heteroaryl,

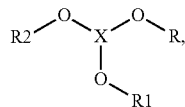
(VIII)

wherein

X is P, S, B or Si,

R is alkenyl or alkynyl and

R1 and R2 are independently from each other H, alkyl, alkenyl, alkynyl, aralkyl, aryl or heteroaryl,

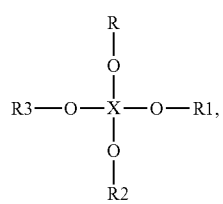
(IX)

wherein

X is P, S, B or Si,

R is alkenyl or alkynyl and

R1, R2 and R3 are independently from each other H, alkyl, alkenyl, alkynyl, aralkyl, aryl or heteroaryl,

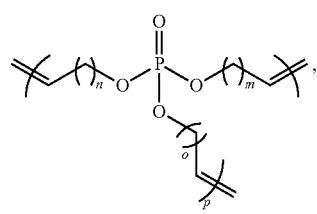
(Xa)

wherein n, m and o are independently from each other an integer between 1 and 20 and p is an integer of 2 or more,

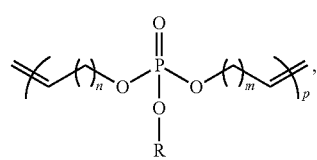
(Xb)

wherein

R is H, alkyl, alkenyl, alkynyl, aralkyl, aryl or heteroaryl, n and m are independently from each other an integer between 1 and 20 and p is an integer of 2 or more or

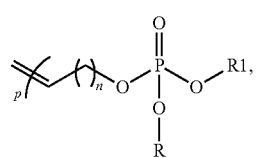
(Xc)

wherein
R and R1 are independently from each other H, alkyl, alkenyl, alkynyl, aralkyl, aryl or heteroaryl,
n is an integer between 1 and 20 and
p is an integer of 2 or more,
wherein the total concentration of all sensitizer compounds is $1 \cdot 10^{-5}$ to $1 \cdot 10^{-3}$ mol/l, the total concentration of all emissive compounds is $1 \cdot 10^{-2}$ to $1 \cdot 10^{-4}$ mol/l and the total content of all sensitizer compounds, all emissive compounds and all compounds capable of reacting with singlet oxygen is at least 90 mol-%.

3. A composition containing:
a) at least one compound capable of reacting with singlet oxygen, and
b) at least one compound, which has a triplet state capable of energy transfer via an emissive process or a non-emissive process, wherein the at least one compound having a triplet state is
   i) at least one phosphorescent compound sufficiently soluble in the compound capable of reacting with singlet oxygen and/or
   ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is capable of a triplet-triplet energy transfer to the at least one emissive compound,
wherein the at least one compound capable of reacting with singlet oxygen comprises at least one terminal unsaturated carbon-carbon bond and is selected from the group consisting of compounds having anyone of the following general formulae (I) to (X):

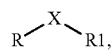
(I)

wherein
X is O or S,
R is alkenyl or alkynyl and
R1 is H, alkyl, ether-alkyl, ether-alkenyl, alkenyl, alkynyl, aralkyl, aryl or heteroaryl,

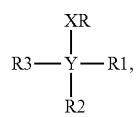
(II)

wherein
X is O or S,
R is alkenyl or alkynyl,
Y is alkyl, alkenyl, alkynyl, aralkyl, aralkenyl, aralkynyl, aryl or heteroaryl and
R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

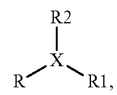
(III)

wherein
X is N or P,
R is alkenyl or alkynyl and
R1 and R2 are independently from each other H, alkyl, alkenyl, alkynyl, aralkyl, aryl or heteroaryl,

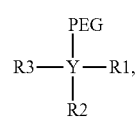
(IV)

wherein
PEG is an oligoethylene glycol or polyethylene glycol group having 2 to 99 ethylene glycol units,
R1 is alkenyl or alkynyl,
Y is Si and
R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

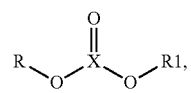
(V)

wherein
X is P, S, B or Si,
R is alkenyl or alkynyl and
R1 is H, alkyl, alkenyl, alkynyl, aralkyl, aryl or heteroaryl,

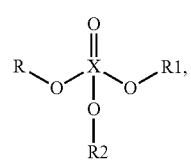
(VI)

wherein
X is P, S, B or Si,
R is alkenyl or alkynyl and
R1 and R2 are independently from each other H, alkyl, alkenyl, alkynyl, aralkyl, aryl or heteroaryl,

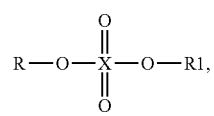
(VII)

wherein
X is P, S, B or Si,
R is alkenyl or alkynyl and
R1 is H, alkyl, alkenyl, alkynyl, aralkyl, aryl or heteroaryl,

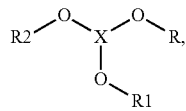
(VIII)

wherein
X is P, S, B or Si,
R is alkenyl or alkynyl and
R1 and R2 are independently from each other H, alkyl, alkenyl, alkynyl, aralkyl, aryl or heteroaryl,

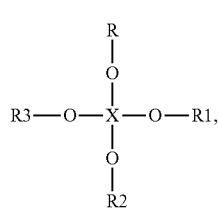
(IX)

wherein
X is P, S, B or Si,
R is alkenyl or alkynyl and
R1, R2 and R3 are independently from each other H, alkyl, alkenyl, alkynyl, aralkyl, aryl or heteroaryl,

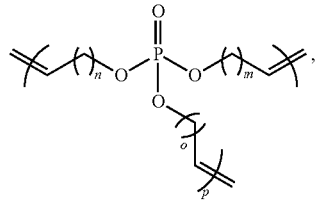
(Xa)

wherein
n, m and o are independently from each other an integer between 1 and 20 and
p is an integer of 2 or more,

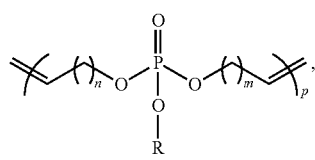
(Xb)

wherein
R is H, alkyl, alkenyl, alkynyl, aralkyl, aryl or heteroaryl,
n and m are independently from each other an integer between 1 and 20 and
p is an integer of 2 or more or

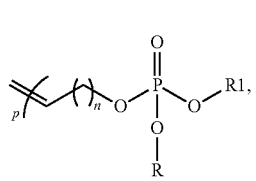
(Xc)

wherein
R and R1 are independently from each other H, alkyl, alkenyl, alkynyl, aralkyl, aryl or heteroaryl,
n is an integer between 1 and 20 and
p is an integer of 2 or more,
wherein the at least one compound having a triplet state capable of energy transfer via an emissive process or a non-emissive process is i) at least one phosphorescent compound that can be sufficiently dissolved in the compound capable of reacting with singlet oxygen.

4. A composition containing:
a) at least one compound capable of reacting with singlet oxygen, and
b) at least one compound, which has a triplet state capable of energy transfer via an emissive process or a non-emissive process, wherein the at least one compound having a triplet state is
  i) at least one phosphorescent compound sufficiently soluble in the compound capable of reacting with singlet oxygen and/or
  ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is capable of a triplet-triplet energy transfer to the at least one emissive compound,
wherein the at least one compound capable of reacting with singlet oxygen comprises at least one terminal unsaturated carbon-carbon bond and is selected from the group consisting of compounds having anyone of the following general formulae (I) to (X):

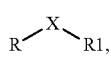
(I)

wherein
X is O or S,
R is alkenyl or alkynyl and
R1 is H, alkyl, ether-alkyl, ether-alkenyl, alkenyl, alkynyl, aralkyl, aryl or heteroaryl,

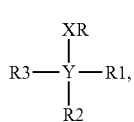
(II)

wherein

X is O or S,

R is alkenyl or alkynyl,

Y is alkyl, alkenyl, alkynyl, aralkyl, aralkenyl, aralkynyl, aryl or heteroaryl and R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

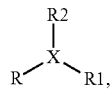

(III)

wherein

X is N or P,

R is alkenyl or alkynyl and

R1 and R2 are independently from each other H, alkyl, alkenyl, alkynyl, aralkyl, aryl or heteroaryl,

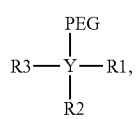

(IV)

wherein

PEG is an oligoethylene glycol or polyethylene glycol group having 2 to 99 ethylene glycol units, R1 is alkenyl or alkynyl, Y is Si and R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

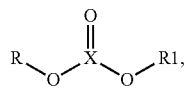

(V)

wherein

X is P, S, B or Si,

R is alkenyl or alkynyl and

R1 is H, alkyl, alkenyl, alkynyl, aralkyl, aryl or heteroaryl,

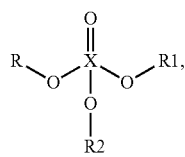

(VI)

wherein

X is P, S, B or Si,

R is alkenyl or alkynyl and

R1 and R2 are independently from each other H, alkyl, alkenyl, alkynyl, aralkyl, aryl or heteroaryl,

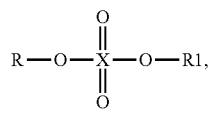

(VII)

wherein

X is P, S, B or Si,

R is alkenyl or alkynyl and

R1 is H, alkyl, alkenyl, alkynyl, aralkyl, aryl or heteroaryl,

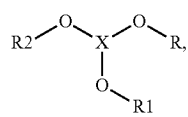

(VIII)

wherein

X is P, S, B or Si,

R is alkenyl or alkynyl and

R1 and R2 are independently from each other H, alkyl, alkenyl, alkynyl, aralkyl, aryl or heteroaryl,

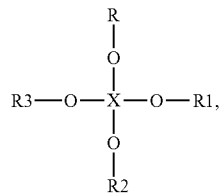

(IX)

wherein

X is P, S, B or Si,

R is alkenyl or alkynyl and

R1, R2 and R3 are independently from each other H, alkyl, alkenyl, alkynyl, aralkyl, aryl or heteroaryl,

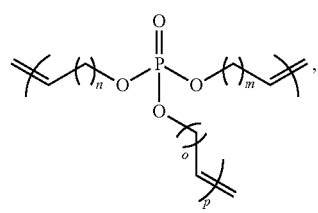

(Xa)

wherein n, m and o are independently from each other an integer between 1 and 20 and p is an integer of 2 or more,

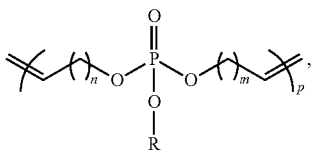 (Xb)

wherein

R is H, alkyl, alkenyl, alkynyl, aralkyl, aryl or heteroaryl, n and m are independently from each other an integer between 1 and 20 and p is an integer of 2 or more or

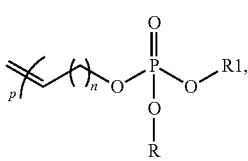 (Xc)

wherein

R and R1 are independently from each other H, alkyl, alkenyl, alkynyl, aralkyl, aryl or heteroaryl, n is an integer between 1 and 20 and p is an integer of 2 or more, wherein the at least one compound having a triplet state capable of energy transfer via an emissive process or a non-emissive process is ii) at least one sensitizer compound being capable of absorbing radiation at a first frequency $v_1$ and at least one emissive compound, wherein the at least one sensitizer compound is capable of transferring energy to the at least one emissive compound and wherein the at least one emissive compound, after obtaining energy transferred from the at least one sensitizer compound, is capable of emitting light at a second frequency $v_2$, wherein the following equation is fulfilled: $v_2 > v_1$, wherein the at least one sensitizer compound is capable of a triplet-triplet energy transfer to the at least one emissive compound.

5. The composition in accordance with claim 4, wherein the at least one emissive compound is capable of a triplet-triplet annihilation.

6. The composition in accordance with claim 4, wherein the at least one compound capable of reacting with singlet oxygen is contained in the composition in such an amount that the number of terminal unsaturated carbon-carbon bonds of the at least one compound capable of reacting with singlet oxygen is at least 100 times higher in the composition than the number of molecules of all compounds having a triplet state capable of energy transfer via an emissive process or a non-emissive process.

7. The composition in accordance with claim 4, wherein the at least one compound capable of reacting with singlet oxygen has the general formula (II), in which X is oxygen, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, Y is $C_{1-6}$-alkyl or phenyl and R1, R2, R3 are independently from each other H and XR, wherein X is oxygen and R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

8. The composition in accordance with claim 4, wherein the at least one compound capable of reacting with singlet oxygen is selected from the group consisting of 3-butene-1-ol, 4-pentene-1-ol, 5-hexene-1-ol, 6-heptene-1-ol, 7-octene-1-ol, 1,2-di-(3-buten-1-yloxy)ethane, 1,2-di-(4-penten-1-yloxy)ethane, 1,2-di-(5-hexen-1-yloxy)ethane, 1,2-di-(6-hepten-1-yloxy)ethane, 1,2-di-(7-octen-1-yloxy)ethane, 1,2-di-(3-buten-1-yloxy)benzene, 1,2-di-(4-penten-1-yloxy)benzene, 1,2-di-(5-hexen-1-yloxy)benzene, 1,2-di-(6-hepten-1-yloxy)benzene, 1,2-di-(7-octen-1-yloxy)benzene, 1,3,5-tri-(3-buten-1-yloxy)benzene, 1,3,5-tri-(4-penten-1-yloxy)benzene, 1,3,5-tri-(5-hexen-1-yloxy)benzene, 1,3,5-tri-(6-hepten-1-yloxy)benzene, 1,3,5-tri-(7-octen-1-yloxy)benzene and arbitrary combinations of two or more of these compounds.

9. The composition in accordance with claim 4, wherein the at least one compound capable of reacting with singlet oxygen has the general formula (III), wherein X is phosphorus, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 and R2 are independently from each other H or selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

10. The composition in accordance with claim 4, wherein the at least one compound capable of reacting with singlet oxygen has the general formula (IV), in which PEG is an oligoethylene glycol or polyethylene glycol group having 2 to 99 ethylene glycol units, R1 is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, Y is Si and R2, R3 are independently from each other H, COOR, XR4 or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, wherein X is N or P and R, R4 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

11. The composition in accordance with claim 4, wherein the at least one compound capable of reacting with singlet oxygen has the general formula (VII), wherein X is S, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 is $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

12. The composition in accordance with claim 4, wherein the at least one compound capable of reacting with singlet oxygen has the general formula (VI), wherein X is P, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 and R2 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

13. The composition in accordance with claim 4, wherein the at least one compound capable of reacting with singlet oxygen has the general formula (VIII), wherein X is B, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 and R2 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

14. The composition in accordance with claim 4, wherein the at least one compound capable of reacting with singlet oxygen has the general formula (IX), wherein X is Si, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1, R2 and R3 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

15. The composition in accordance with claim 4, wherein the at least one compound capable of reacting with singlet oxygen is one according to the general formula (Xa), wherein n, m and o are independently from each other an integer between 1 and 10 and p is an integer of 2 to 120.

16. The composition in accordance with claim 15, wherein the at least one compound capable of reacting with singlet oxygen is one according to the subsequent formulae (XI) to (XIV):

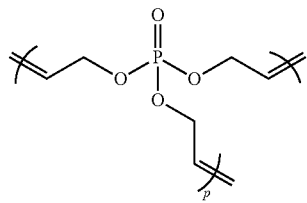

(XI)

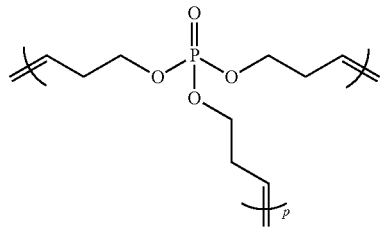

(XII)

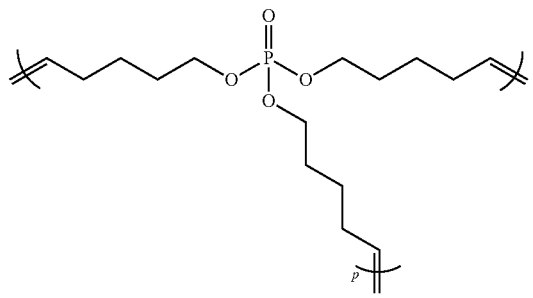

(XIII)

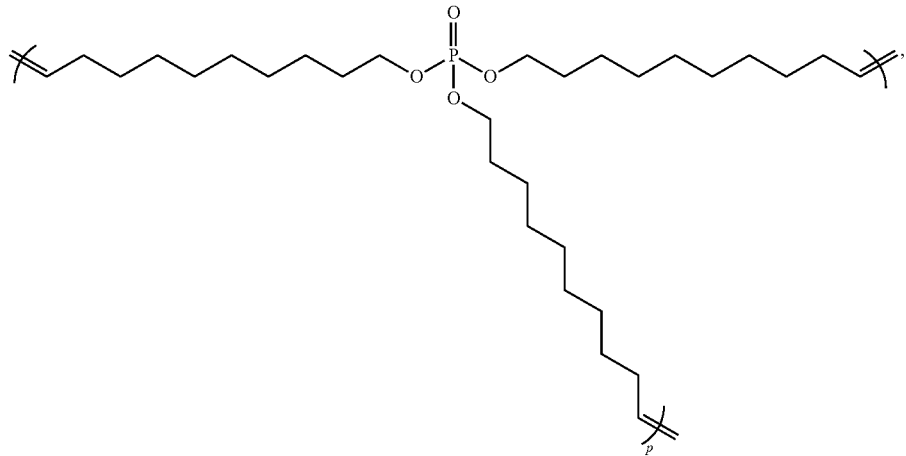

(XIV)

wherein in each of these formulae p is an integer of 2 to 120.

* * * * *